(12) United States Patent
Shanmugam et al.

(10) Patent No.: US 11,559,627 B2
(45) Date of Patent: Jan. 24, 2023

(54) AUTOINJECTOR WITH A NEEDLE COVER

(71) Applicant: WOCKHARDT LIMITED, Maharashtra (IN)

(72) Inventors: Loganathan Shanmugam, Bangalore (IN); Jayant Shrikant Karajgi, Aurangabad (IN); Suresh Kumar Natarajan, Bangalore (IN); Vasanthan Mani, Bangalore (IN); Cyril Lourdnathan Joseph Fernandez, Wayanad (IN)

(73) Assignee: WOCKHARDT LIMITED, Aurangabad (IN)

( * ) Notice: Subject to any disclaimer, the term of this patent is extended or adjusted under 35 U.S.C. 154(b) by 582 days.

(21) Appl. No.: 16/486,403

(22) PCT Filed: Aug. 21, 2018

(86) PCT No.: PCT/IB2018/056312
§ 371 (c)(1),
(2) Date: Aug. 15, 2019

(87) PCT Pub. No.: WO2019/043502
PCT Pub. Date: Mar. 7, 2019

(65) Prior Publication Data
US 2021/0138153 A1    May 13, 2021

(30) Foreign Application Priority Data
Sep. 4, 2017    (IN) .............................. 201721031188

(51) Int. Cl.
*A61M 5/315* (2006.01)
*A61M 5/32* (2006.01)
*A61M 5/20* (2006.01)

(52) U.S. Cl.
CPC .......... *A61M 5/20* (2013.01); *A61M 5/31581* (2013.01); *A61M 5/3202* (2013.01); *A61M 2005/2073* (2013.01)

(58) Field of Classification Search
CPC ............ A61M 5/31581; A61M 5/3202; A61M 5/3272; A61M 5/2033; A61M 5/3257;
(Continued)

(56) References Cited

U.S. PATENT DOCUMENTS 6,767,336 B1 * 7/2004 Kaplan ................. A61M 5/326
604/131
6,805,686 B1   10/2004 Fathallah et al.
(Continued)

FOREIGN PATENT DOCUMENTS

CA    2996232 A1    3/2017
EP    3 106 193 A1  12/2016
(Continued)

*Primary Examiner* — Tasnim Mehjabin Ahmed
(74) *Attorney, Agent, or Firm* — Maschoff Brennan

(57) ABSTRACT

The invention relates to an autoinjector 59 for administering a fluid medicament to a subject comprising: a housing 1 for receiving a cartridge holder; a driver assembly 8; the driver assembly on actuation may move the cartridge 3 forward in the cartridge holder 2; a needle cover 4 may be coupled to the housing wherein the needle cover 4 travels in a linear or translational movement; said needle cover 4 is adapted to protect a needle when the needle cover may be in first locking position 17 and second locking position 18; the linear or translational movement may be achieved by a cam profile 13 and a cam follower 14; the cam profile 13 may be provided on outside surface of housing and the cam follower 14 located between the needle cover 4 and the housing 1; a first biasing member 15; and a second biasing member 16 configured to bias the cartridge 3 and the needle cover 4 respectively; and a safety cap 11 to control the actuation of the autoinjector. The needle cover 4 further comprises a
(Continued)

sleeve 91 or sleeve 92 which prevents or inhibits the obstruction of the movement of needle cover 4 when the user accidentally hold the needle cover 4 during actuation of the autoinjector.

15 Claims, 33 Drawing Sheets

(58) Field of Classification Search
CPC .. A61M 2005/2073; A61M 2005/3247; A61M 2005/3267
See application file for complete search history.

(56) References Cited

U.S. PATENT DOCUMENTS

| | | | |
|---|---|---|---|
| 7,357,790 B2 * | 4/2008 | Hommann | A61M 5/326 |
| | | | 604/198 |
| 7,449,012 B2 | 11/2008 | Young et al. | |
| 8,617,119 B2 | 12/2013 | Liversidge | |
| 2006/0189933 A1 | 8/2006 | Alheidt et al. | |
| 2016/0271331 A1 | 9/2016 | Kraft et al. | |
| 2018/0161516 A1 * | 6/2018 | Wittland | A61M 5/326 |

FOREIGN PATENT DOCUMENTS

| | | | |
|---|---|---|---|
| WO | 93/13819 A1 | 7/1993 | |
| WO | 2016/193349 A1 | 12/2016 | |

\* cited by examiner

AUTOINJECTOR WITH A NEEDLE COVER

PRIORITY DOCUMENT

This application claims priority from the Indian provisional patent application IN 201721031188 filed on Sep. 4, 2017, which is incorporated herein by reference in its entirety for all purposes.

FIELD

The application relates to an autoinjector for administering a fluid medicament to a subject.

BACKGROUND

Many people have 'needle phobia' and are apprehensive of seeing a needle during medicament administration. As a result, people with 'needle phobia' may not regularly administer medicament as prescribed or may improperly administer an injection due to their apprehension.

Following documents disclose autoinjector with needle protection system:

U.S. Pat. No. 6,767,336 discloses autoinjector with a sharp protector that is manually or automatically deployable.

U.S. Pat. No. 7,449,012 discloses autoinjector with a needle cover at least partially received within the housing.

U.S. Pat. No. 6,805,686 discloses autoinjector with extendible needle protector shroud.

U.S. Pat. No. 8,617,119 discloses a safety device having a tubular support for a needle mount end and a protective shield slidably mounted on the support.

SUMMARY

Autoinjector is used to inject a dose of medicament which is contained in a container. It delivers the medicament through a needle. The container includes a cartridge or a pre filled syringe and the like.

Some embodiments disclose an autoinjector for a medicament administration comprising: a housing having a proximal portion and a distal portion; a cartridge holder received within the housing; the cartridge holder having a proximal end and a distal end; an opening at the distal end; a cartridge; a plunger; a needle cover, wherein the housing is at least partially received within the needle cover; the autoinjector further comprises a needle cover locking mechanism, wherein the needle cover locking mechanism comprises a cam profile and a cam follower, wherein the cam follower of locking mechanism is located between the needle cover and the distal portion of the housing in both first locking position and second locking position.

Some embodiments disclose an autoinjector for a medicament administration comprising: a housing having a proximal portion and a distal portion, a cartridge holder received within the housing; the cartridge holder is having a proximal end and a distal end; an opening at the distal end; a cartridge; the housing is having a first sleeve section and second sleeve section; the first sleeve section is having an inward transverse projections on the inner surface; a plunger; the plunger is having two wings provided on the outer surface; a needle cover, wherein the housing is at least partially received within the needle cover; the auto injector further comprises a needle cover locking mechanism; wherein the needle cover locking mechanism comprises a cam profile, a cam follower; wherein the cam follower of the locking mechanism is located between the needle cover and the second sleeve section of the housing in both first locking position and second locking position; wherein the distal surfaces of the wings of the plunger engage the surface of the inward transverse stopping projections of the housing at the end of the medicament administration.

An autoinjector for administering a fluid medicament to a subject comprising: a housing having a proximal portion and a distal portion, a cartridge holder received within the housing, the cartridge holder is having a proximal end and a distal end; an opening at the distal end; a cartridge; the housing is having a first sleeve section; first sleeve section is having inward transverse projections on the inner surface; a plunger; the plunger is having two wings provided on the outer surface; a needle cover, wherein the housing is at least partially received within the needle cover; the needle cover further comprises a sleeve; the auto injector further comprises a needle cover locking mechanism; wherein the needle cover locking mechanism comprises a cam profile; and a cam follower; wherein the cam follower of locking mechanism is located between the needle cover and the second sleeve section of the housing in both first locking position and second locking position; wherein the distal surfaces of the wings of the plunger engage the surface of the inward transverse stopping projection of the housing at the end of the medicament administration.

An autoinjector for administering a fluid medicament to a subject comprising: a housing having a proximal portion and a distal portion, a cartridge holder received within the housing, the cartridge holder is having a proximal end and a distal end; an opening at the distal end; a cartridge; the housing is having a first sleeve section; first sleeve section is having inward transverse projections on the inner surface; a plunger; the plunger is having two wings provided on the outer surface; a needle cover, wherein the housing is at least partially received within the needle cover; the needle cover further comprises a sleeve; the auto injector further comprises a needle cover locking mechanism; wherein the needle cover locking mechanism comprises a cam profile; and a cam follower; wherein the cam follower of locking mechanism is located between the needle cover and the second sleeve section of the housing in both first locking position and second locking position; wherein the distal surfaces of the wings of the plunger engage the surface of the inward transverse stopping projection of the housing at the end of the medicament administration.

Some of the examples disclose the proximal portion of the housing; wherein the housing is having a first sleeve section; a first shoulder at the distal end of the first sleeve section; a second sleeve section extends distally from the first shoulder in the distal portion.

Some of the examples disclose a cartridge holder; wherein the cartridge holder is having slots provided on the proximal portion of the cartridge holder; openings are provided on the outer surface of the cartridge holder.

Some of the examples disclose the cam profile which comprises an angled contour surface in the proximal portion and cylindrical contour surface in the distal portion of the housing.

Some of the examples disclose the cam follower which comprises a cam follower protrusion on the distal portion; a cam follower button on the proximal portion; and a cam follower body extending between them.

Some examples disclose a needle cover further comprising a sleeve, wherein the sleeve is provided on the outer surface of the needle cover.

Some examples disclose a sleeve comprising a proximal end, a distal end and a coil body extending between them.

Some examples disclose a sleeve comprising a proximal end, a distal end and a tubular body extending between them.

Some examples disclose a needle cover comprising a sleeve and a needle cover bottom; the sleeve comprises an inner sleeve and an outer sleeve.

Some of the examples disclose the autoinjector comprising the medicament selected from epinephrine or dihydroergotamine.

BRIEF DESCRIPTION OF THE DRAWINGS

FIG. 25 B is a side view of FIG. 25A showing an a sleeve 92 provided over a needle cover and the needle cover is in the first locking/initial position.

DETAILED DESCRIPTION

The present application relates to an autoinjector for administering a fluid medicament to a subject.

As used herein, the proximal end of a component or component in an assembled autoinjector or the assembled autoinjector is the end that may correspond towards safety cap end. Distal end of a component or component in an assembled autoinjector or the assembled autoinjector may be the end that may correspond to the delivery end or towards the needle cover.

As used herein, the rearward end of a component or component in an assembled autoinjector or the assembled autoinjector is the end that may correspond towards safety cap end. Forward end of a component or component in an assembled autoinjector or the assembled autoinjector may be the end that may correspond to the delivery end or towards the needle cover.

As already described above a need was felt for an autoinjector with an improved needle protection system that may be easily used by a subject.

It may be advantageous if the needle is in a safe location before and after the use to prevent accidental injury or contamination.

The autoinjector with a needle protection system may include a needle cover to move towards the injection end over the needle once the injection of the medicament is completed. The movement of the needle cover with respect to the needle may often be triggered by a spring in an automatic way when the autoinjector is withdrawn from the injection site. In general, the needle cover may be locked in its "after use" position to a locking system.

Figure 1:
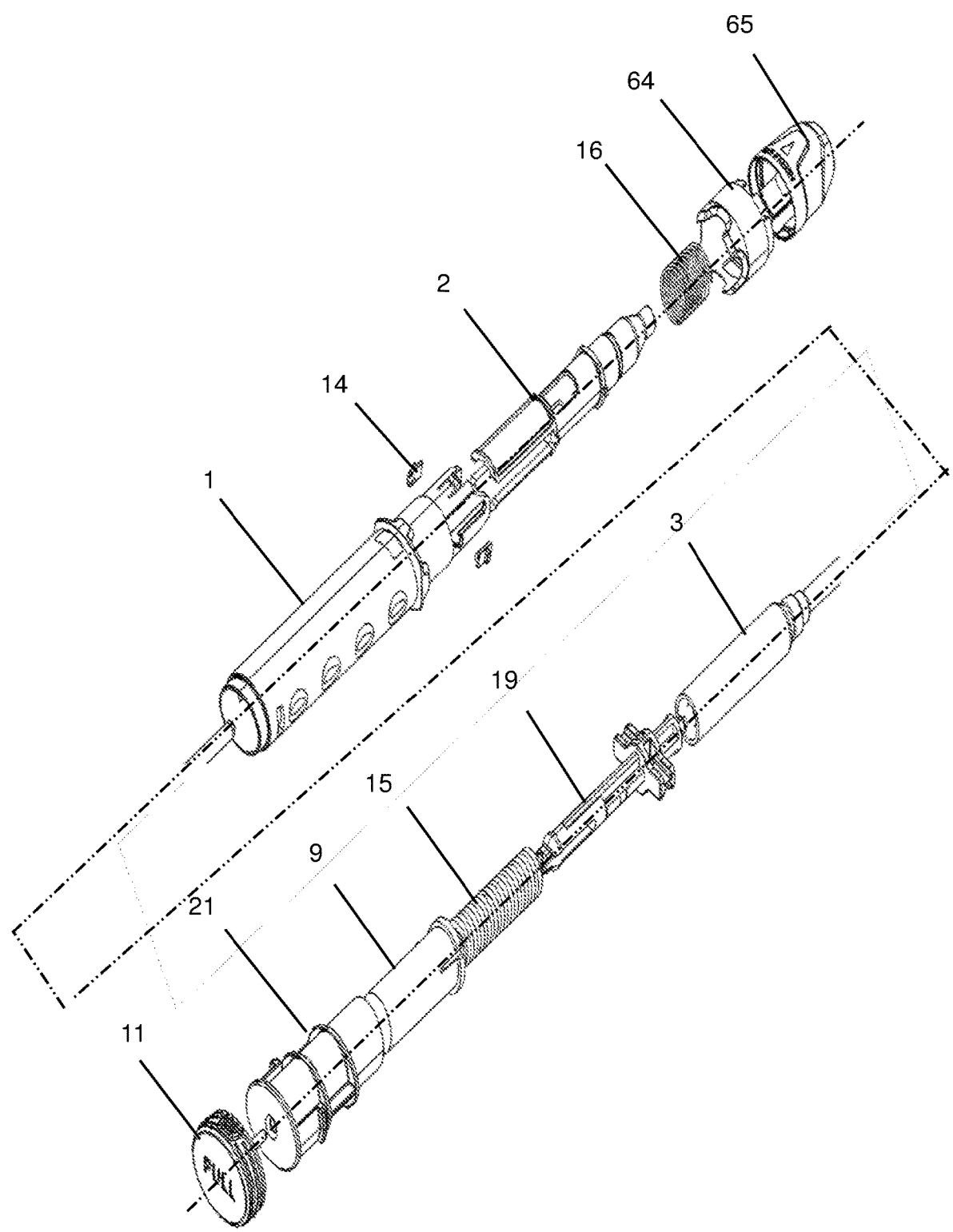
FIG. 1 is an exploded view of an embodiment of an autoinjector.

Some embodiments of an autoinjector 59 may be described with reference to FIG. 1 to FIG. 13 as follows. FIG. 1 gives an exploded view of some of the embodiments of an autoinjector 59. The autoinjector comprises a housing 1, a cartridge holder 2, a top cover 21, a safety cap 11, a collet 9, a first biasing member 15 associated with the cartridge movement and medicament administration, a second biasing member 16 associated with the needle cover locking mechanism 60 during the operation and medicament administration, a needle cover 4 comprising a needle cover top 64, a needle cover bottom 65, a plunger 19 provided with two oppositely located wings 68, 68a towards the distal portion on its outer surface, a cartridge 3 and a needle sheath 7 over the needle 5.

Some of the embodiments of an autoinjector 59 comprises a driver assembly 8; a first biasing member 15; a second biasing member 16; a safety cap 11; and a top cover 21; the first biasing member 15 configured to bias the driver assembly 8; the drive assembly 8 comprises a collet 9 and a collapsible lock 10, a plunger 19.

Needle cover locking mechanism 60 may be described by referring to FIG. 2, FIG. 3A, FIG. 3B and FIG. 3C that disclose an autoinjector 59 for a medicament administration comprises: a housing 1 having a proximal portion and a distal portion, said proximal portion of housing 1 is having a first sleeve section 22, a first shoulder 23 at the distal end of the first sleeve section 22, a second sleeve section 25 extends distally from the first shoulder 23 towards the distal portion of housing 1; a cartridge holder 2 is received within the housing 1; the cartridge holder 2 is having a proximal end and a distal end; the cartridge holder 2 is having an opening at the distal end; a cartridge 3; a plunger 19; a needle 5 fixed to the distal end of the cartridge 3; a needle cover 4, wherein the housing 1 is at least partially received within the needle cover 4; the autoinjector further comprises a needle cover locking mechanism 60 having a first locking position 17 and a second locking position 18; and the needle cover locking mechanism 60 comprises a cam profile 13, and a cam follower 14; the cam follower 14 of locking mechanism 60 is located between the needle cover 4 and the second sleeve section 25 of the housing 1 in both first locking position 17 and second locking position 18. The cam profile 13 may be provided as a pair 13a, 13b which are arranged in diametrically opposite directions on outer surface of the housing 1; similarly cam follower 14 may be provided as a pair 14a, 14b received in the corresponding cam profiles 13a,13b and located between the needle cover 4 and the housing 1.

In the first locking position 17, the needle cover 4 is in the retracted position and in the second locking position 18, the needle cover 4 is in the extended position.

Figures 3A, 3B, 3C:
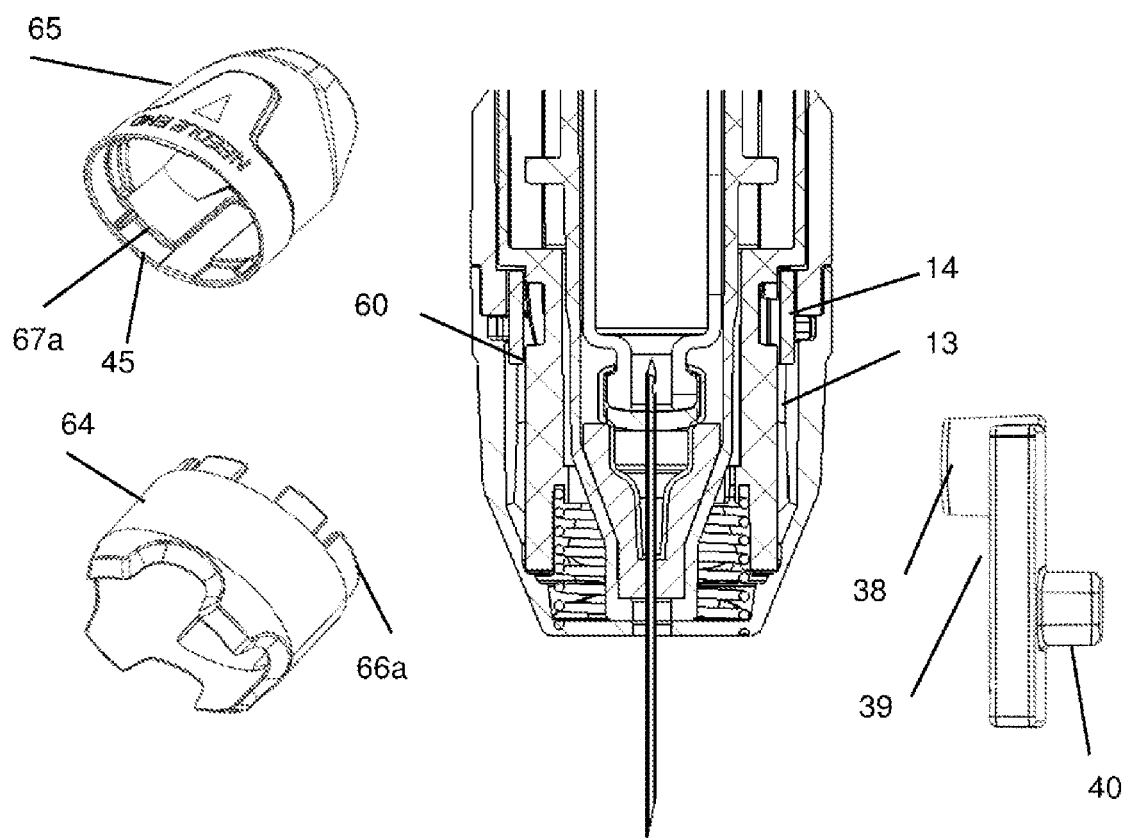
FIG. 3A shows perspective view of needle cover top and needle cover bottom.
FIG. 3B shows front view of cam follower.
FIG. 3C shows cross-sectional view of position of the cam follower on the second sleeve section of the housing after actuation and before needle cover extension.

The autoinjector 59 for a medicament administration comprises a needle cover locking mechanism 60. FIG. 3A shows a perspective view of the needle cover top 64 and the needle cover bottom 65; FIG. 3B shows a front view of the cam follower 14; FIG. 3C shows sectional view of position of the cam follower 14 on the second sleeve section 25 of the housing 1 after actuation and before needle cover 4 extension; Referring to FIG. 3B and FIG. 3C, the needle cover 4 of the locking mechanism 60 may comprise a cam profile 13 on outside surface of the second sleeve section 25 and a cam follower 14. The cam follower 14 of the locking mechanism 60 may be located between the needle cover 4 and the second sleeve section 25 of the housing 1 in both the first locking position 17 and the second locking position 18. The needle cover 4 may be of cylindrical, oval or elliptical shape. The needle cover 4 may be considered to be made up of a proximal portion needle cover top 64 and a distal portion needle cover bottom 65. There may be provided a plurality of projections 66a on the needle cover top 64 towards the distal portion. The projections 66a may be over the entire circumference. There may be ribs 67a provided over the inner surface of the needle cover bottom 65 towards the proximal portion. The circumferential diameter of the outer surface of the plurality of projections 66a can be slightly smaller than the circumferential diameter of the inner surface of the proximal portion of the needle cover bottom 65 as to make a firm snap fit between the needle cover top 64 and needle cover bottom 65. Further the distal end of the plurality of projections 66a abut the proximal end of the ribs 67a to indicate that both needle cover top 64 and needle cover bottom 65 have firmly snapped up. Alternatively, the needle cover top 64 and needle cover bottom 65 may be ultrasonically welded. There may be a needle cover groove 45 that runs on the inner surfaces of both needle cover top 64 and needle cover bottom 65 and positioned in an aligned manner. The purpose of the needle cover groove 45 may be to provide a path for the cam follower protrusion 40 of the cam follower 14 to traverse both during the actuation and medicament administration.

Figure 4:
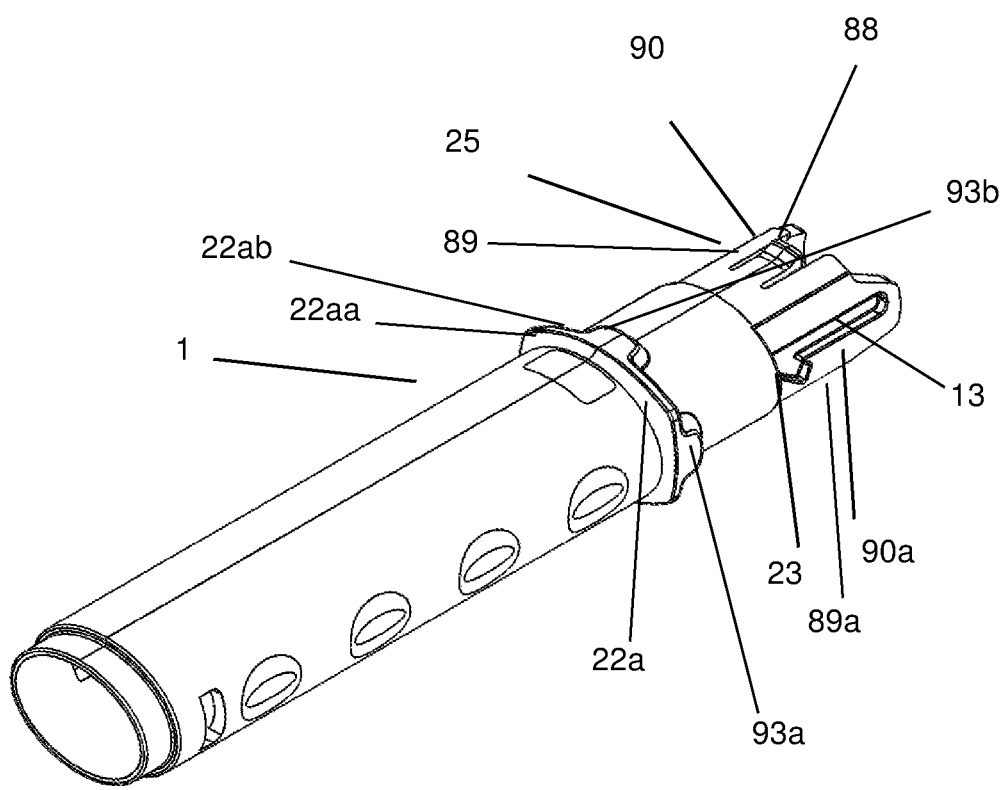
FIG. 4 shows a perspective view of the details of the housing.

FIG. 4 shows a perspective view of the housing 1. Referring FIG. 4, the housing 1 may comprise a proximal portion and a distal portion. The proximal portion of the housing 1 may have a first sleeve section 22. A first shoulder 23 may be formed at the distal end of the first sleeve section 22. The first shoulder 23 may be due to reduced diameter of the housing 1 extending in the inward direction. A second sleeve section 25 may extend in the distal direction from the end of the first shoulder 23. The housing 1 of FIG. 4 may be of cylindrical, oval or elliptical shape. The first sleeve section 22 at the proximal end is having end surface to receive the safety cap 4 and the distal portion is having a circumferential peripheral ridge 22a. The peripheral ridge 22a may be positioned proximal to first shoulder 23. The peripheral ridge 22a is having front end 22aa and rear end 22ab portions, whereas the first sleeve section 22 is affixed into the front end portion 22*aa* and the second sleeve section 25 is extending from the rear end portion 22*ab*. At the rear end 22*ab*, a pair of diametrically opposed rectangular shaped like projection heads 93*a*, 93*b*, 93*c*, 93*d* extending downwardly on the surface of second sleeve section 25. The peripheral ridge may facilitate sliding of needle cover 4.

Figure 2:
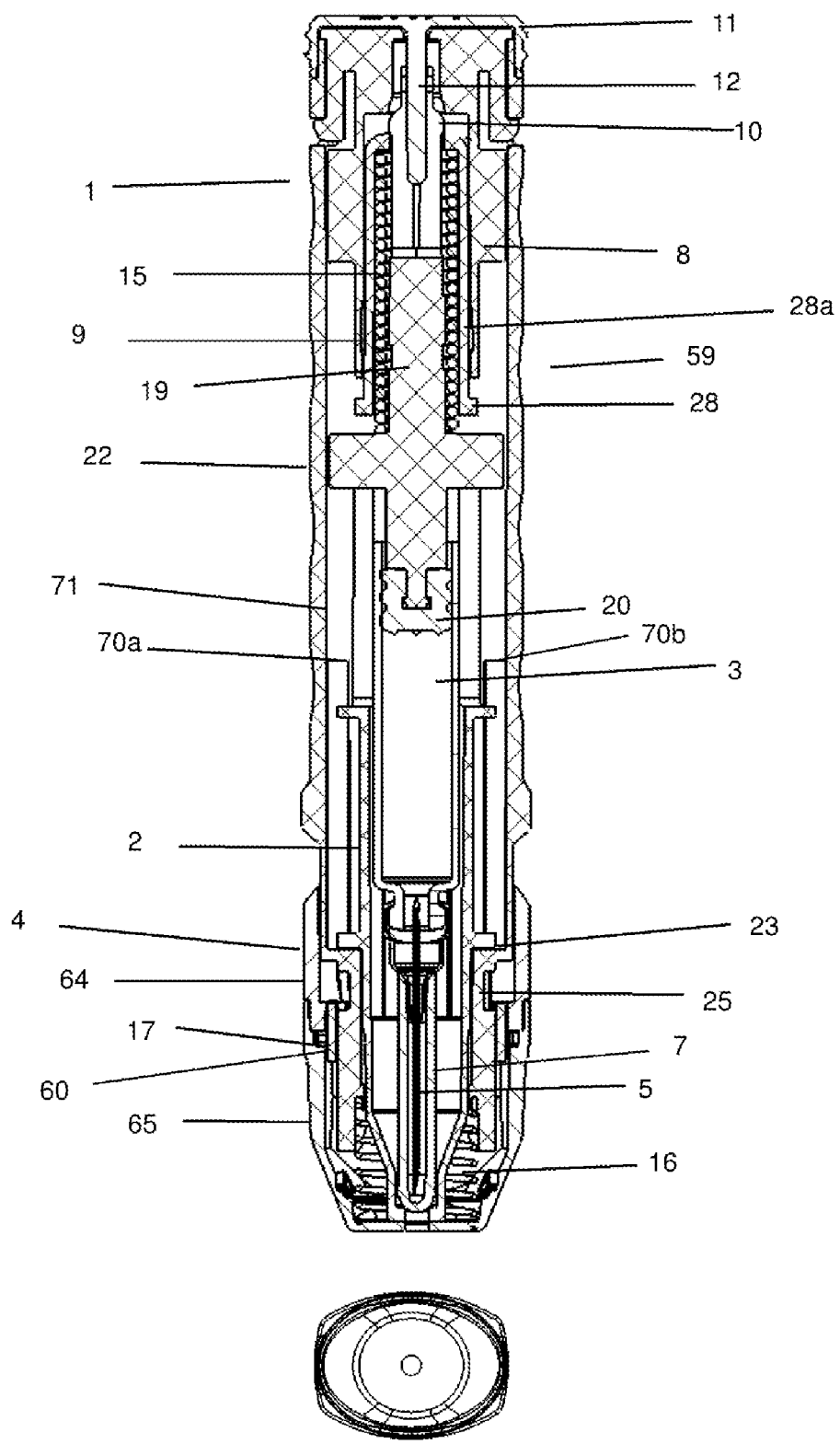
FIG. 2 is a longitudinal view and bottom view of an autoinjector with a needle cover in the first locking position with structural details in a cross sectional view.

There may be plurality of inward transverse projections extending from the inner surface 71 of the housing 1 towards the distal portion. Referring to FIG. 2, in the preferred embodiment the first sleeve section 22 of the housing 1 may be having an inward transverse projections 70*b*, 70*a* extending from the inner surface 71 of the housing. The inward transverse projections 70*b*, 70*a* may be provided in diametrically opposite directions. The inward transverse projections 70*b*, 70*a* may be rectangular in shape.

Some of the examples of an autoinjector 59 disclose wherein the second sleeve section 25 at distal end comprises a diametrically opposite cutting arms 89, 89*a* having flank surfaces 90, 90*a* as shown in FIG. 4.

Some of the examples of an autoinjector 59 disclose wherein second sleeve section 25 comprises locking projections 88, 88*a* diametrically opposite to flank surfaces 90, 90*a* of cutting arms 89, 89*a* as shown in FIG. 4.

Some of the examples of an autoinjector 59 disclose wherein flank surfaces 90, 90*a* of cutting arms 89, 89*a* comprises cam profile 13 as shown in FIG. 4.

Figure 5:
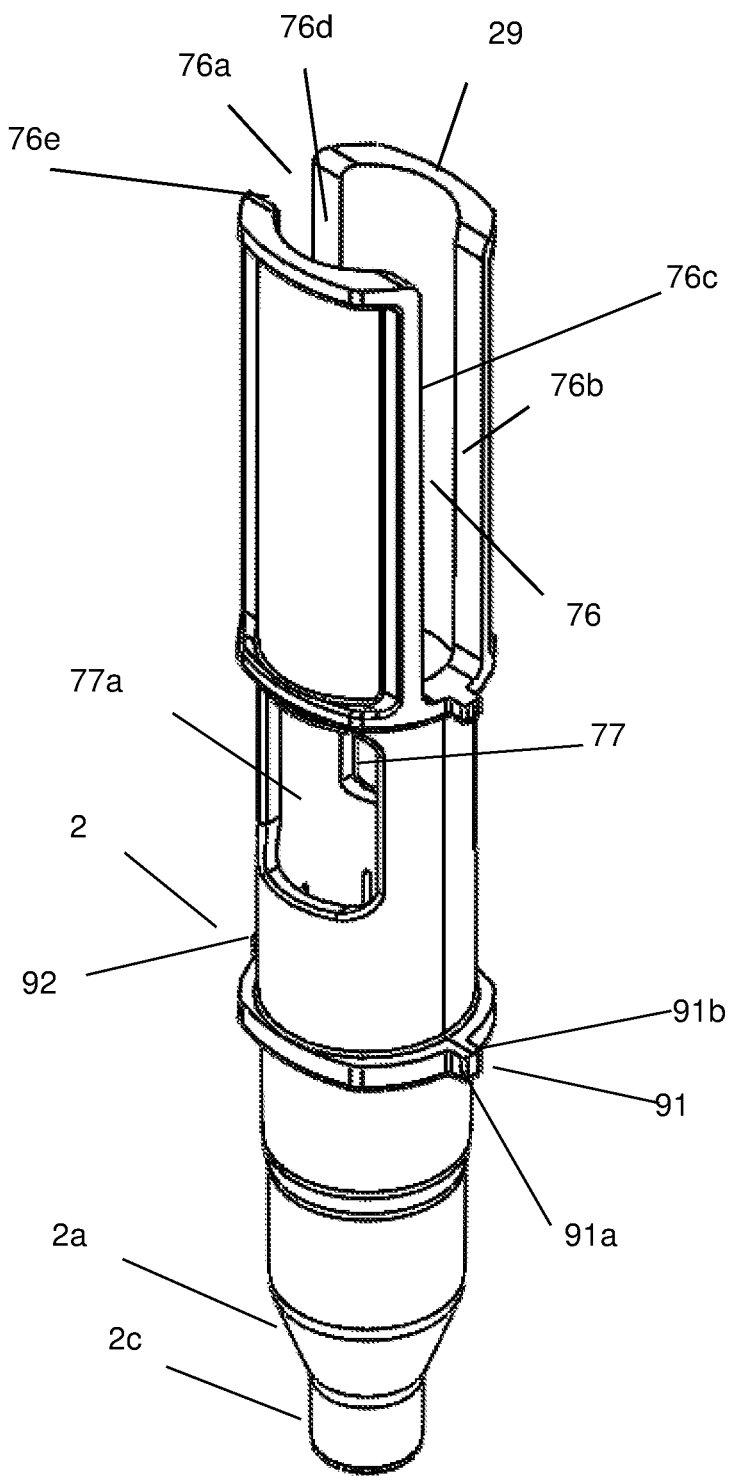
FIG. 5 shows perspective view of the cartridge holder of the auto injector.

Referring to FIG. 5 that describe the cartridge holder 2, in some of the embodiments of an autoinjector wherein slots 76, 76*a* may be formed on the proximal portion of the cartridge holder 2 carved out of the surface of the cartridge holder 2. The slots 76, 76*a* may be positioned diametrically opposite. The slot 76 may have two opposite surfaces 76*b*, 76*c*. Similarly the slot 76*a* may have two opposite surfaces 76*d*, 76*e*. There may be diametrically opposite openings 77, 77*a* distal to the slots 76, 76*a* as shown in FIG. 5 positioned on the cartridge holder 2. The distal portion of the cartridge holder 2 may have conical portion 2*a* and further distal to it a reduced diameter cylindrical portion 2*c*. The cartridge holder 2 may have plurality of ledges 91,92 provided towards the distal portion. In one of the preferred embodiments the cartridge holder 2 may have on the distal portion diametrically opposite ledges 91, 92 provided on the outer surface. Each of the ledges 91, 92 may be described as follows. The ledge 91 may have been formed due to two parallel projections 91*a*, 91*b* spaced apart. The shape of the projections 91*a*, 91*b* may be rectangular one. Similarly ledge 92 may have been formed due to two parallel projections 92*a*, 92*b* spaced apart. The thickness of inward transverse projections 70*b*, 70*a* of the housing 1 is smaller than the gap between the two projections 91*a*, 91*b*. Hence the inward transverse projection 70*b* is allowed to pass through the spatial gap between the projections 91*a*, 91*b* of ledge 91. Similarly inward transverse projection 70*a* is allowed to pass through the spatial gap between the projections 92*a*, 92*b* of ledge 92. This feature of traverse of the inward transverse projections 70*b*, 70*a* of the housing 1 in the spatial gap between the projections 91*a*, 91*b* of ledge 91 and the projections 92*a*, 92*b* of ledge 92 allow proper alignment of the cartridge holder 2 and the housing 1.

Some examples of the autoinjector disclose wherein the cartridge holder 2 is having slots 76, 76*a* provided on the proximal portion of the cartridge holder 2; openings 77, 77*a* are provided on the outer surface of the cartridge holder 2 as shown in FIG. 5.

Some examples of the autoinjector disclose wherein the slots 76, 76*a* are having four surfaces 76*b*, 76*c*, 76*d* and 76*e* as shown in FIG. 5.

Some examples of autoinjector 59 disclose wherein the distal closed end of the cartridge holder 2 abuts the inside surface of needle cover 4 in the first locking position 17.

Figure 6:
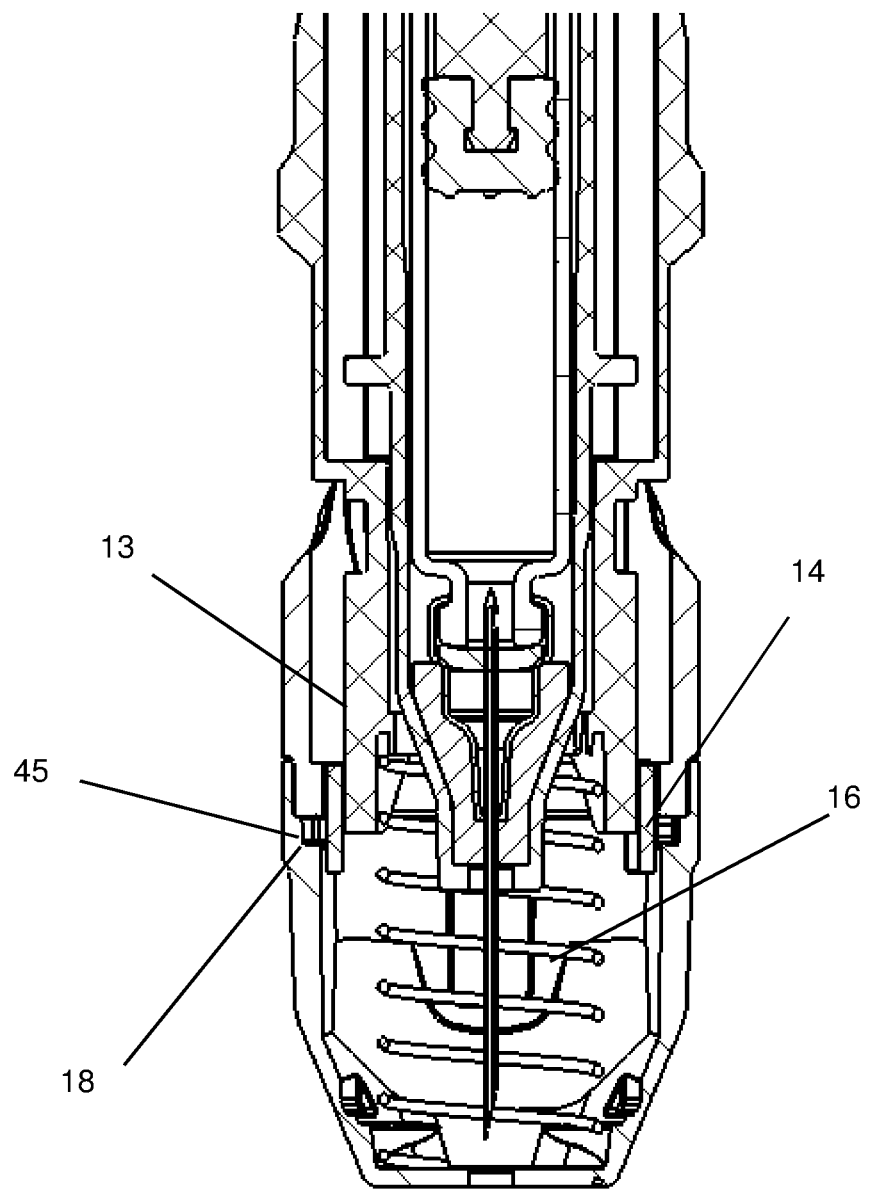
FIG. 6 shows the position of the cam follower on the housing of an auto injector after needle cover extension.

FIG. 6 shows the position of the cam follower 14 on the second sleeve section 25 of the housing 1 of an autoinjector 59 after needle cover 4 extension in the second locking position 18.

Figure 7:
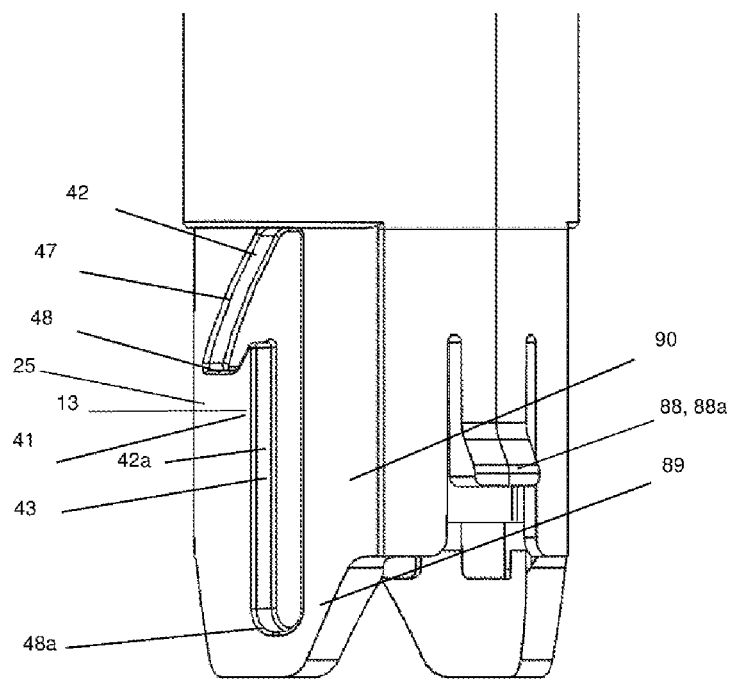
FIG. 7 shows a schematic view of cam profile on the housing.

Details of the cam profile 13 on the surface of second sleeve section 25 of housing are described in FIG. 7. Referring to FIG. 7 and FIG. 3B the cam profile 13 provided on the outer surface of second sleeve section 25 on the distal portion of the housing 1 may be described as follows. An angled contour surface 41 of the cam profile 13 may have a frustum of a cone contour surface 42 in the proximal portion and cylindrical or rectangular contour surface 42*a* towards the distal portion. The distal portion of frustum of contour surface 48 is shown in FIG. 7. Cam profile 13 may be formed out as a groove 43 in the housing to facilitate engagement or coupling of cam follower button 38, on to housing 1. The Cam profile 13 may be formed out as a protrusion on the housing 1 to facilitate engagement or interaction of cam follower button 38, on to housing 1. The engagement or interaction may be by snap fit, a butt joint, a bayonet coupling, welding or other methods of attachment.

Figure 8:
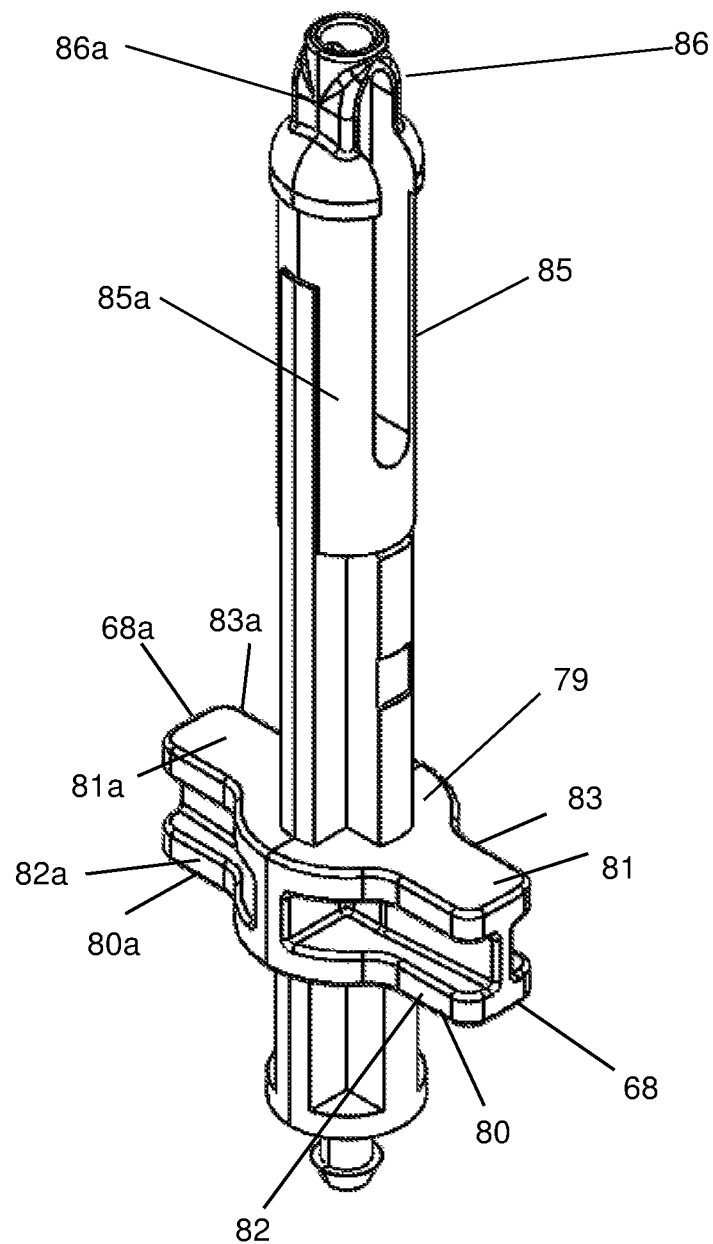
FIG. 8 shows a perspective view of the plunger.

The plunger 19 details may be described with reference to FIG. 8. Referring to FIG. 8, diametrically opposite wings 68, 68*a* have been provided on the distal portion of the plunger 19 on the outer surface. The wings 68, 68*a* may also be known as the left wing 68 and the right wing 68*a*. The wings 68, 68*a* may be a sort of a diametrically opposite protrusions extending from a circular flange 79 like structure in the distal portion of the plunger 19. The wings 68, 68*a* may be of any geometrical shape such as rectangular, circular, square and trapezoidal and the like. The wings 68, 68*a* shown in FIG. 8 may be of rectangular shape with a distal surfaces 80, 80*a* and proximal surfaces 81, 81*a*. Wings 68, 68*a* having a rectangular shape may also have two opposite side surfaces 82, 83 connecting the distal and proximal surfaces for the left wing 68 and 82*a*, 83*a* for the right wing 68*a*. The proximal portion of the plunger 19 may have two diametrically opposite longitudinal blades 85, 85*a*. The proximal portion of the longitudinal blades 85, 85*a* may have collapsible lock potion 86, 86*a*. It may be that the collapsible lock portion 86, 86*a* may have the appearance of a frustum of a cone and the like.

Figure 9:
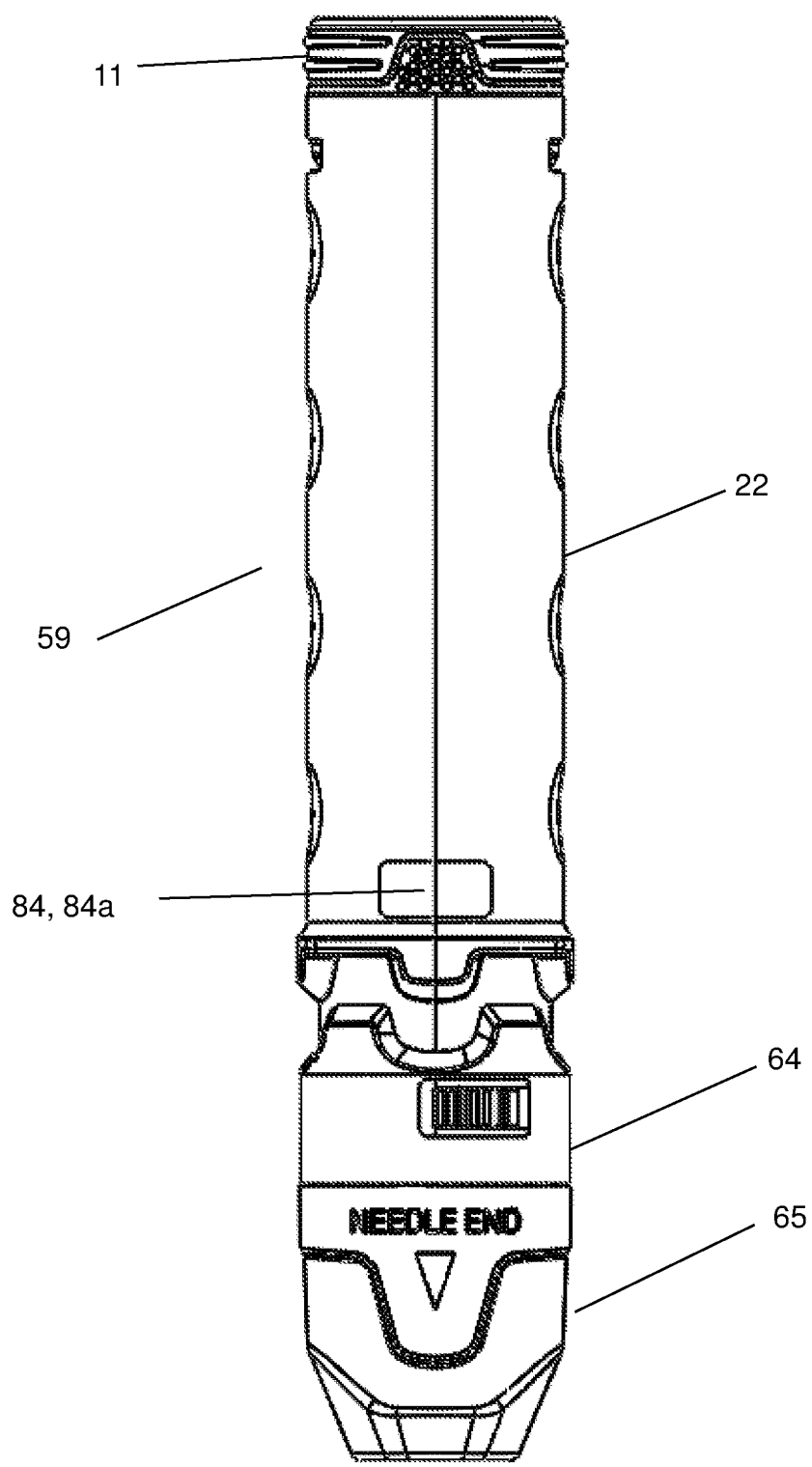
FIG. 9 shows a perspective view of the autoinjector with safety cap in place.

FIG. 9 shows a front view of an autoinjector 59 with safety cap 11 in place. In some of the embodiments, windows 84, 84*a* may be provided on the outer surface of the first sleeve section 22 of the housing 1. Window 84*a* may be located in a diametrically opposite position. In some of the embodiments, windows 84, 84*a* may be provided on the outer surface of the first sleeve section 22 towards the distal portion of the housing 1.

The working of the autoinjector 59 may further be illustrated referring FIG. 5, FIG. 8, FIG. 9 to FIG. 13 and FIG. 2. In the initial position the safety cap 11 may be in the proximal end of the autoinjector 59 mounted over the housing 1 as shown in FIG. 9. In this initial position the medicament may be visible through the windows 84, 84*a* on the outer surface of the housing 1 and due to the openings 77, 77*a* on the cartridge holder 2. The windows 84, 84*a* on the outer surface of the housing 1 may be formed by virtue of the unwrapped label over the transparent housing 1 portion corresponding to the shape of window. The transparent windows 84, 84*a* and the openings 77, 77*a* may be in an alignment. The purpose of the window 84, 84*a* may be to ensure visibility of stopper 20 on completion of medicament administration. The safety pin 12 of the safety cap 11 may pass through the top cover 21 central aperture 52. The positioning of the safety pin 12 inside the central aperture 52 may prevent the collapsible lock portion 86, 86*a* of the plunger 19 access to the frusto conical cam surface 58 of the top cover 21. Further the collapsible lock portion 86, 86*a* of the plunger 19 may be locked with the collet 9 by the first biasing member 15. This can help the autoinjector 59 to be on a non-activated position. Further insertion of safety cap 11 through the collapsible snap lock 10 may prevent accidental unlocking of the drive assembly 8. In the initial position, the needle cover top 64 and needle cover bottom 65 of the needle cover 4 may be biased by the second biasing member 16. The second biasing member 16 may be biased from the housing 1. The distal end of the cylindrical portion of the cartridge holder 2 may have an engagement with the proximal end of the inner surface of the cover bottom 65. The engagement may be a simple butt joint. However, the proximal end 29 of the cartridge holder 2 does not have any engagement with the collet 9. The collet comprises cylindrical section 28*a* from proximal end to distal end and a distal flange 28. There may be a gap between the proximal end of the cartridge holder 2 and the collet 9 as shown in FIG. 2.

Figure 10:
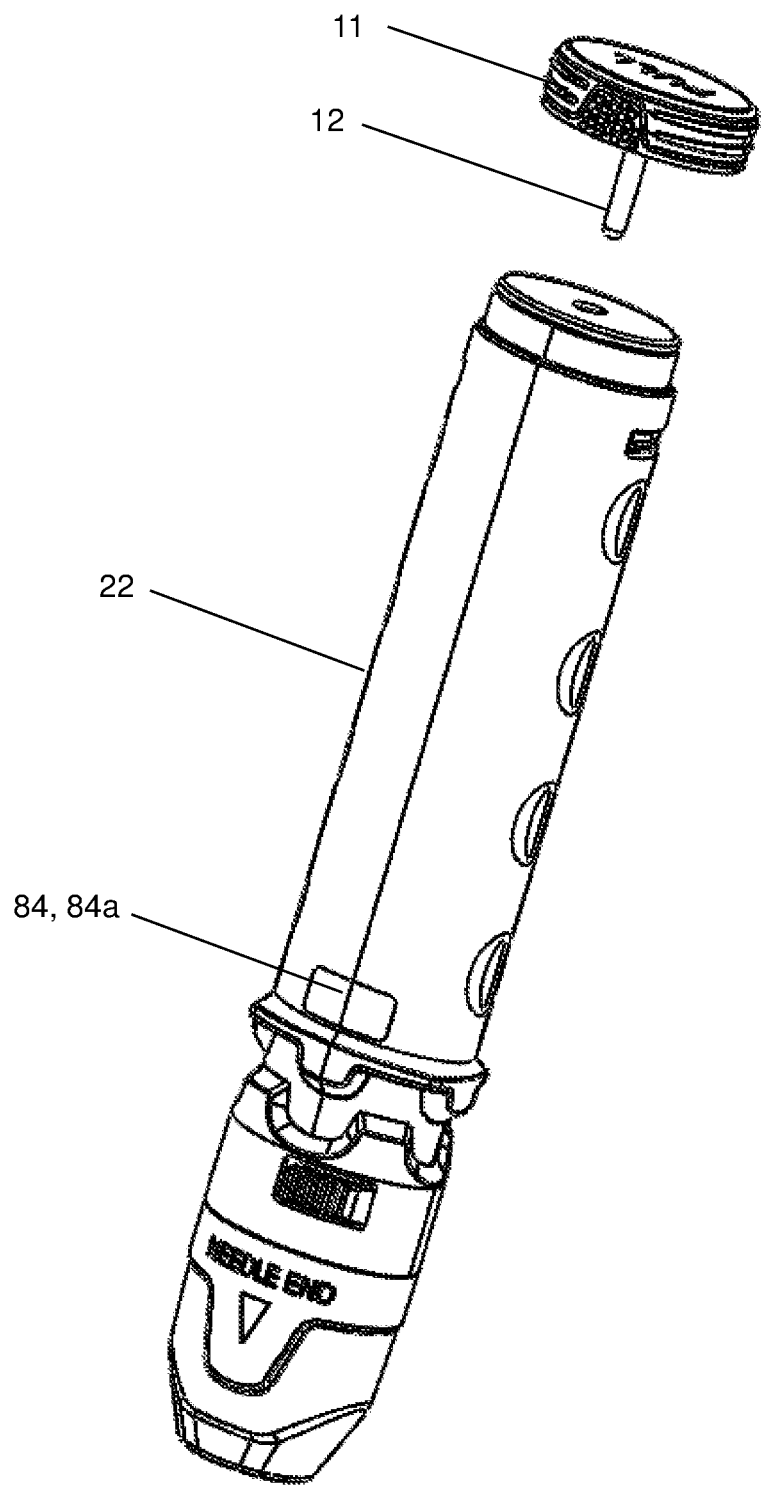
FIG. 10 shows a perspective view of the autoinjector with safety cap removed.

FIG. 10 shows a perspective view of the autoinjector 59 with safety cap 11 removed. To actuate the autoinjector 59, the next step is to pull out the safety cap 11 by holding the ridges of the safety cap 11. This action may place the autoinjector 59 in an activating position as a result of collapsible lock portion 86, 86*a* of the plunger 19 (Shown in FIG. 8) finding access to the frusto conical cam surface 58 (shown in FIG. 12) of the top cover 21.

Figure 11:
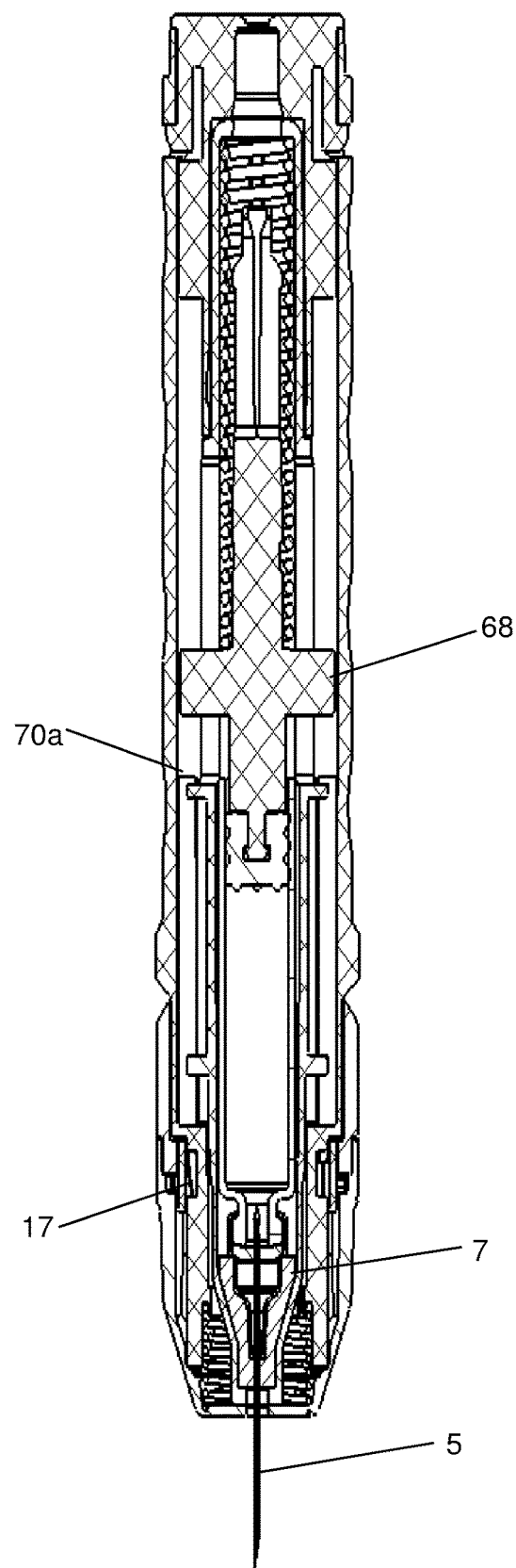
FIG. 11 shows a sectional view of the autoinjector with needle exposed from the needle cover bottom before medicament administration.

FIG. 11 shows a sectional view of the autoinjector 59 with needle 5 exposed from the needle cover bottom 65 of the needle cover 4 before the medicament administration. After the safety cap 11 is removed the user may hold the autoinjector 59 first sleeve section 22 of the housing 1 in the hand and press the needle cover bottom 65 on to the body for actuation. The needle cover bottom 65 and needle cover top 64 of the needle cover 4 may move in the proximal direction towards the housing 1 and may push the cartridge holder 2 backward due to the butt joint between the needle cover bottom 65 and the cartridge holder 2 and butt against the collet 9. The cartridge holder 2 may push back the collet 9 due to the butt joint between the needle cover 4 and the cartridge holder 2 which in turn may push the collapsible lock portion 86, 86*a* to release the first biasing member 15. The first biasing member 15 and the second biasing member 16 may be spring. The collapsible lock portion 86, 86*a* may move inward through the chamfer provided on the top cover 21 resulting in unlocking of the collet 9 of the drive assembly 8 and collapsible lock 10 of the plunger 19. The first biasing member 15 may relax and hold the collet 9 against the top cover 21 at the proximal end and may push the cartridge 3 along with the needle on the distal end. As a consequence the needle 5 may get enough force from the first biasing member 15 to pierce the needle sheath 7, clothing of the patient and finally though the skin. While the needle cover bottom 65 and the needle cover top 64 may be pushed against the housing 1, the cam follower 14 may move along the cam profile angled contour surface 41 and may occupy the proximal position. The cam follower 14 may have both rotational and linear movement with respect to the needle cover bottom 65 and needle cover top 64 of the needle cover 4 while the needle cover 4 may have only linear motion.

The needle sheath 7 is positioned over the needle 7 such that the open end of the sheath fits over and around the needle 5. The length of the sheath 7 is such that its closed end is slightly beyond or spaced from the end of needle 5. The cartridge 3 moves forward whereby the needle sheath 7 is compressed the most between the cartridge holder 2 and the cartridge 3. At this juncture, the cartridge 3 may move forward and the distal surface of the cartridge 3 may have an engagement with the proximal surface of the compressed needle sheath 7.

Some of the examples of autoinjector 59 disclose wherein the proximal end of the cartridge holder 2 abuts the distal end of the collet 9 on actuation of the autoinjector 59 by pressing the needle cover 4 against the body after the removal of the safety cap 12 due to backward movement of the cartridge holder 2.

Some of examples of an autoinjector 59 disclose wherein the top cover 21 inner surface is having a chamfer shape; the collapsible lock 10 is having a collapsible lock portion 86, 86*a* towards the proximal end; the collapsible lock portion 86, 86*a* moves inward through the chamfer on actuation of the autoinjector 59 by pressing the needle cover 4 against the body after the removal of the safety cap 12 due to backward movement of the cartridge holder 2 resulting in unlocking of the collet 9 and collapsible lock 10 of the plunger 19.

Figure 12:
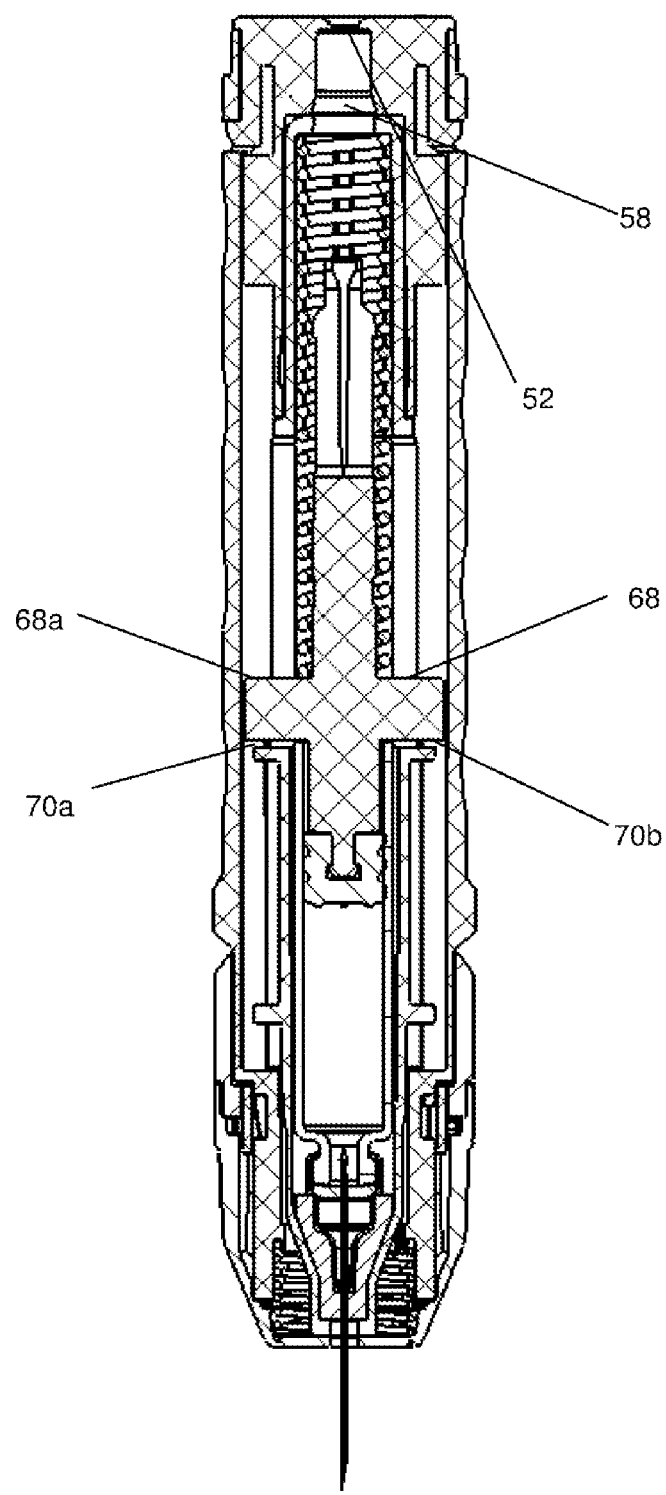
FIG. 12 shows a sectional view of the autoinjector with needle exposed from the needle cover bottom after medicament administration.

FIG. 12 shows a sectional view of the autoinjector 59 with needle 5 exposed from the needle cover bottom 65 after medicament administration. Once the needle 5 may be pierced into the skin of the patient, due to the spring force of the first biasing member 15 the plunger 19 may move forward and may deliver the pre-defined volume of medicament through the needle 5. The plunger 19 may move from the position with respect to the housing 1 as shown in FIG. 11 and the distal surface 80 of the left wing 68 of the plunger 19 and distal surface 80*a* of the right wing 68*a* of the plunger 19 may engage the proximal surface of the inward transverse projections 70*b*, 70*a* of the first sleeve section 22 of the housing 1 thus preventing the plunger 19 from hitting the cartridge 3 surface, inducing no stress on the cartridge 3. During this stage the stopper 20 may move toward the distal end and the stopper 20 position may correspond with the window 84, 84*a* provided on the distal portion of the first sleeve section 22 of the housing 1 and thus providing a visual indication for the user that the medicament is delivered.

Some of the examples of an autoinjector disclose wherein the distal surfaces 80, 80*a* of the left wing 68 and right wing 68*a* of the plunger 19 engage the surface of the inward transverse projection 70*b*,70*a* of the housing 1 at the end of the medicament administration; contacting surfaces 82, 83 of left wing 68 engage with the surfaces of the slots 76*c*, 76*b* of the cartridge holder 2; and contacting surfaces 82*a*, 83*a* of right wing 68*a* engage with the surfaces of the slots 76*e*, 76*d* of the cartridge holder 2. FIG. 8 and FIG. 12 may be referred for details.

Figure 13:
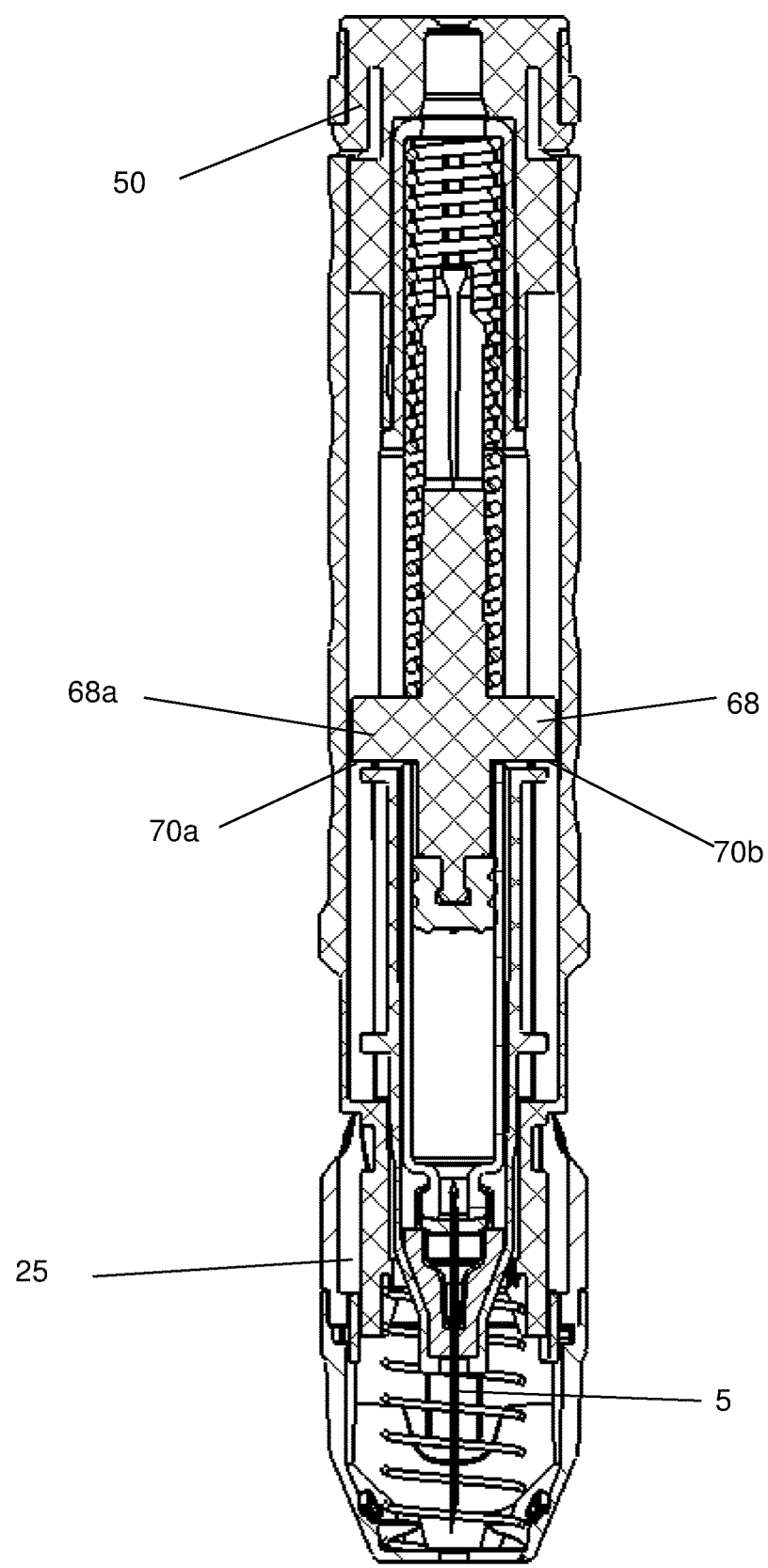
FIG. 13 shows a sectional view of the autoinjector with needle cover top and needle cover bottom in extended position protecting the exposed needle after medicament administration.

FIG. 13 shows a sectional view of the autoinjector 59 with needle cover top 64 and needle cover bottom 65 of the needle cover 4 in extended position protecting the exposed needle 5 after the medicament administration. After the medicament may be delivered, the autoinjector 59 may be held against the body for the desired period before the autoinjector 59 may be withdrawn from the body. Simultaneously, the needle cover 4 comprising needle cover top 64 and needle cover bottom 65 may extend forward due to the tension of the second biasing member 16. The cam follower 14 may follow the cylindrical contour surface 42*a* of the cam profile 13. Referring FIG. 7, the cylindrical contour surface 42a being longer than cam profile angled contour surface 41 the longer travel of the cam follower 14 leading to longer extension of the needle cover 4. During this stage the needle cover 4 may extend forward and may get locked with the housing 1 at the second locking position 18. There may also be a fool-proof locking of the needle cover 4 with housing 1 such that both forward and backward movement of needle cover 4 may be restricted.

The cam profile 13 may be provided on the outer surface of second sleeve section 25 on the distal portion of the housing 1. An angled contour 41 of cam profile 13 have in the proximal portion, a frustum of a cone contour 42 and cylindrical contour 42a towards the distal portion. The distal portion of contour surface 42a shown in FIG. 7 may be a cylindrical one. Cam profile 13 may be formed out as a groove 43 in the housing to facilitate a coupling of cam follower button 38, on to housing 1. The interaction may be by snap fit, a bayonet coupling or other methods of attachment that may facilitate free movement of the cam follower button 38. Further the protrusion 40 of the cam follower 14 may mate with groove 45 on the inner surface of the needle cover 4 both in the first locking position 17 and the second locking position 18. Distal portion of cam follower body is shown by numeral 40. It may be considered that groove 45 (refer FIG. 3A and FIG. 6) on the inner surface of the needle cover 4 traverses both in the needle cover top 64 and the needle cover bottom 65. The advantage thereof may be that the protrusion 40 provided over the width of the cam follower 14 component may establish effective operable connection to the corresponding groove 45 provides better stability between the needle cover 4 and second sleeve section surface 25 of the housing 1.

Projections 88, 88a may be provided on the distal portion of the second sleeve section 25 of the housing 1. Projection corresponding to numeral 88 is shown in FIG. 7 whereas the opposite projection numeral 88a is not shown. Fool proof locking of the needle cover 4 may be achieved by the abutment of projections 88, 88a provided on the second sleeve section 25 towards the distal end with the diametrically opposite grooves 87a, 87b provided on the inner surface of the needle cover top 64 due to the force of the relaxation of the second biasing member 16.

Some of the embodiments of autoinjector 59 disclose wherein the cam profile 13 comprises an angled contour surface 47 in the proximal portion and cylindrical contour surface 42a in the distal portion.

Some of the embodiments of autoinjector disclose wherein the cam follower button 38 of the cam follower 14 mates with cylindrical contour surface 48a of the cam profile 13 in the second locking position 18.

An autoinjector 59 for administering a fluid medicament to a subject comprising: a housing 1 having a proximal portion and a distal portion; a cartridge holder 2 received within the housing 1; the cartridge holder 2 is having a proximal end and a distal end; an opening at the distal end; a cartridge 3; a plunger 19; a needle cover 4, wherein the housing 1 is at least partially received within the needle cover 4; the autoinjector 59 further comprises a needle cover locking mechanism 60 having a first locking position 17 and a second locking position 18; wherein the needle cover locking mechanism 60 comprises a cam profile 13; and a cam follower 14; and wherein the cam follower 14 of locking mechanism 60 is located between the needle cover 4 and the distal portion of the housing 1 in both first locking position 17 and second locking position 18.

Some of the embodiments of autoinjector 59 disclose wherein various medicaments may be administered. Some of the embodiments of the autoinjector 59 are particularly suitable for the administration of medicaments such as dihydroergotamine or epinephrine.

Some embodiments of an autoinjector 59 may be described with reference to FIG. 14 and FIG. 15 as follows. The autoinjector 59 of FIG. 14 comprises a housing 1, the housing 1 having a proximal portion and a distal portion, said proximal portion of housing is having a first sleeve section 22, a first shoulder 23 at the distal end of the first sleeve section 22, a second sleeve section 25 extends distally from the first shoulder 23 in the distal portion, a second shoulder 24 at the distal end of the second sleeve section 25, a third sleeve section 26 extends distally from the second shoulder 24, a third shoulder 62 at the distal end of the third sleeve section 26, a fourth sleeve section 61 extends distally from the distal end of the third shoulder 62; a cartridge holder 2 is received within the housing 1; cartridge holder 2 is having a proximal end and a distal end; the cartridge holder 2 is having an opening at the distal end; a cartridge 3; a plunger 19; a needle 5 fixed to the distal end of the cartridge 3; a needle cover 4, wherein the housing 1 is at least partially received within the needle cover 4; the autoinjector 59 further comprises a needle cover locking mechanism 60 having a first locking position 17 and a second locking position 18; and the needle cover locking mechanism 60 comprises a cam profile 13; a cam follower 14; the cam follower 14 of locking mechanism 60 is located between the needle cover 4 and the fourth sleeve section 61 of the housing 1 in both first locking position 17 and second locking position 18.

The cam profile 13 may be provided on the outer surface of fourth sleeve section 61 on the distal portion of the housing 1. Some of the examples of autoinjector 59, comprising a pair of diametrically opposite cam profiles 13a, 13b on the distal portion of the housing 1. A pair of cam followers 14a, 14b received on the corresponding cam profiles 13a, 13b and positioned between the needle cover 4 and the housing 1.

Figure 14:
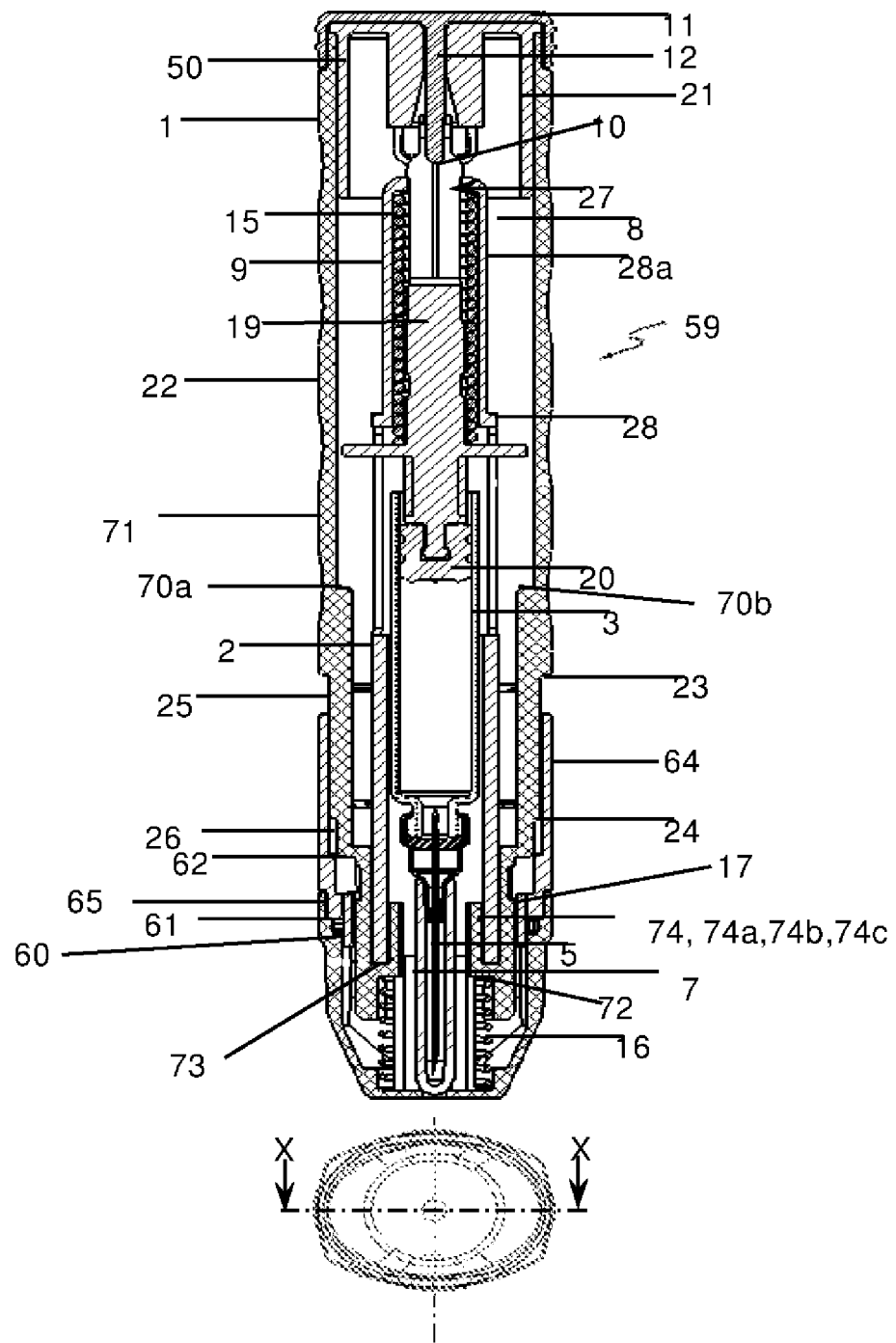
FIG. 14 is a longitudinal view and bottom view of another embodiment of an autoinjector with a needle cover in the first locking position with structural details in a cross sectional view along line x-x.
Figure 15:
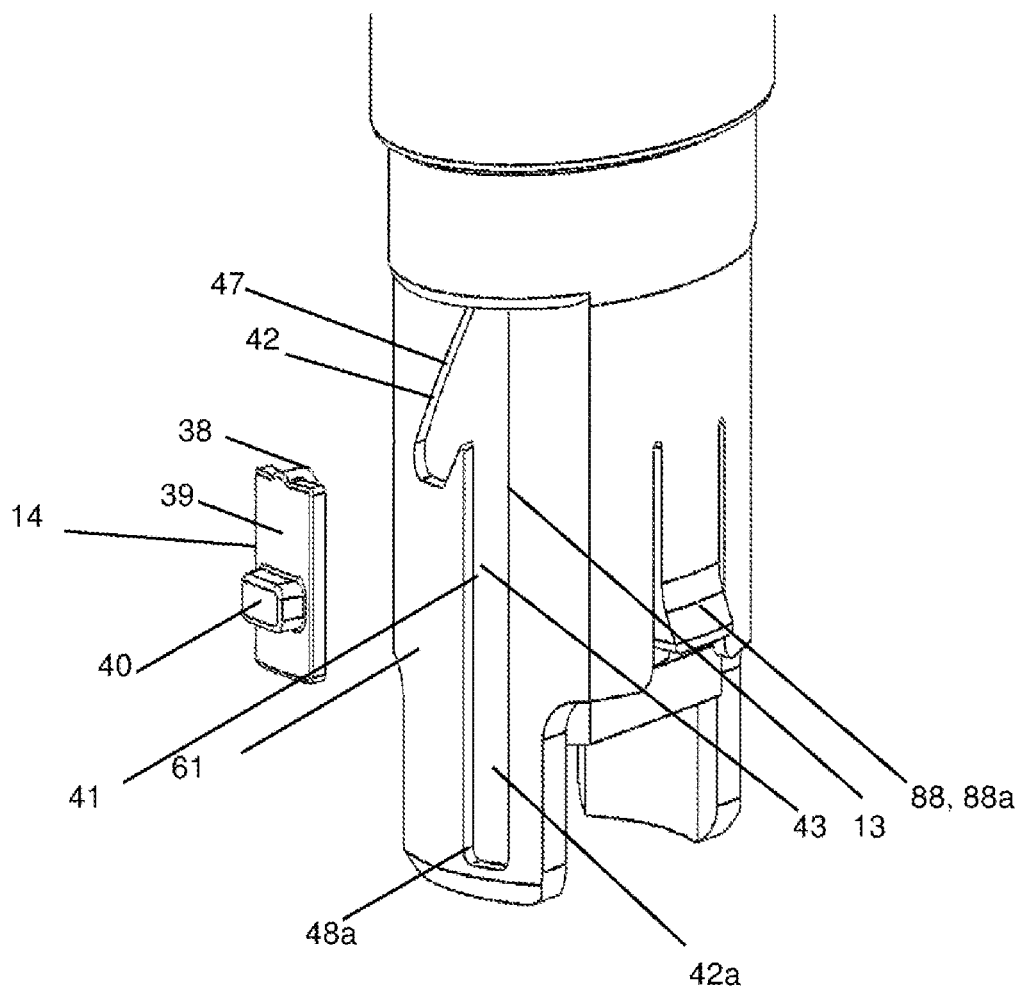
FIG. 15 shows side exploded view of the cam follower and cam profile on the fourth sleeve section of housing of another embodiment of the autoinjector.

The needle cover may comprise a needle cover top 64 and needle cover bottom 65 like in the embodiment of FIGS. 1 to 13; cam follower 14 of the needle cover locking mechanism 60 and the position of the cam follower 14 on the fourth sleeve section 61 of the housing in some of the embodiments of an autoinjector is shown in FIG. 14 and FIG. 15.

Referring FIG. 14, the first sleeve section 22 of the housing 1 may be having an inward transverse projection 70b, 70a extending from the inner surface 71 of the housing 1. As referred in aforementioned embodiments of FIGS. 1-13, the plunger 19 provided with two oppositely located wings 68,68a. The wings 68,68a of plunger 19 engaged with the inward transverse projection 70a,70b of housing 1, the plunger 19 is prevented from hitting the cartridge 3 surface and no stress occurs on the cartridge 3.

Referring FIG. 14, the fourth sleeve section 61 of the housing 1 may have the following configuration. A shoulder 72 may extend internally from the distal portion of the fourth sleeve section 61 in the transverse direction. Further from the inner surface 73 of the shoulder 72, there may be two or more protrusions extend in the transverse direction towards the proximal portion from the inner surface 73 of the shoulder 72. In some of the embodiments as shown in FIG. 14, there are four protrusions 74, 74a, 74b and 74c extending in the transverse direction. The length of the protrusion 74 controls the forward movement of cartridge 2 within the cartridge holder 3. The length of the protrusion 4 can be increased to restrict the forward movement of cartridge 2, hence the less amount of medicament will be delivered to the subject.

Furthermore, the structural changes may be carried out on both the cartridge holder 2 and the housing 1. In the initial position the medicament may be visible through the windows on the outer surface of the housing 1 and the openings on the cartridge holder 2 like in the embodiment of FIGS. 1 to 13. The working of the autoinjector 59 involves removal of safety cap, actuation on the body surface of the patient and removal of the autoinjector from the body surface accompanied by the needle cover extension as explained in the embodiments of FIGS. 1 to 13.

FIG. 15 is a side exploded view of locking mechanism 60 comprising the cam follower 14 and cam profile 13 provided on the fourth sleeve section 61 of housing. Referring FIG. 15, the cam follower 14 may comprise a cam follower protrusion 40 in the distal portion, a cam follower body 39 extending towards proximal portion and a cam follower button 38 in the proximal portion. The cam follower protrusion 40 and cam follower button 38 may be located on opposite surfaces of the cam follower body 39. The shape of the cam follower protrusion 40 and cam follower button 38 may be cylindrical, conical, square, rectangular, trapezoid and the like.

The cam profile 13 may be provided on the outer surface of fourth sleeve section 61 on the distal portion of the housing 1. An angled contour surface 41 of the cam profile 13 may have in the proximal portion a frustum of a cone contour 42 and/or a cylindrical or a rectangular contour 42a towards the distal portion. The distal portion of contour surface 42a shown in FIG. 15 may be a cylindrical one. Cam profile 13 may be formed out as a groove 43 in the housing to facilitate interaction or engagement of cam follower button 38, on to the housing 1. The interaction between the cam profile 13 and cam follower button 38 may be by a snap fit, a bayonet coupling or other methods of attachment that may facilitate free movement of the cam follower button 38 on the cam profile 13. Further the protrusion 40 of the cam follower 14 may mate with groove 45 (as in embodiment of FIGS. 1 to 13) on the inner surface of the needle cover 4 both in the first locking position 17 and the second locking position 18. It may be considered that groove 45 on the inner surface of the needle cover 4 traverses both in the needle cover top 64 and the needle cover bottom 65. The advantage thereof may be that the protrusion 40 provided over the width of the cam follower 14 component may establish effective operable connection to the corresponding groove 45 provide better stability between the needle cover 4 and the fourth sleeve section 61 of the housing.

Projections 88, 88a may be provided on the distal portion of the fourth sleeve section 61 of the housing 1. Projection corresponding to numeral 88 is shown in FIG. 15 whereas the opposite projection numeral 88a is not shown. Fool proof locking of the needle cover 4 may be achieved by the abutment of projections 88, 88a provided on the second sleeve section 25 towards the distal end with the diametrically opposite grooves 87a, 87b provided on the inner surface of the needle cover top 64 due to the force of the relaxation of the second biasing member 16.

Figure 16:
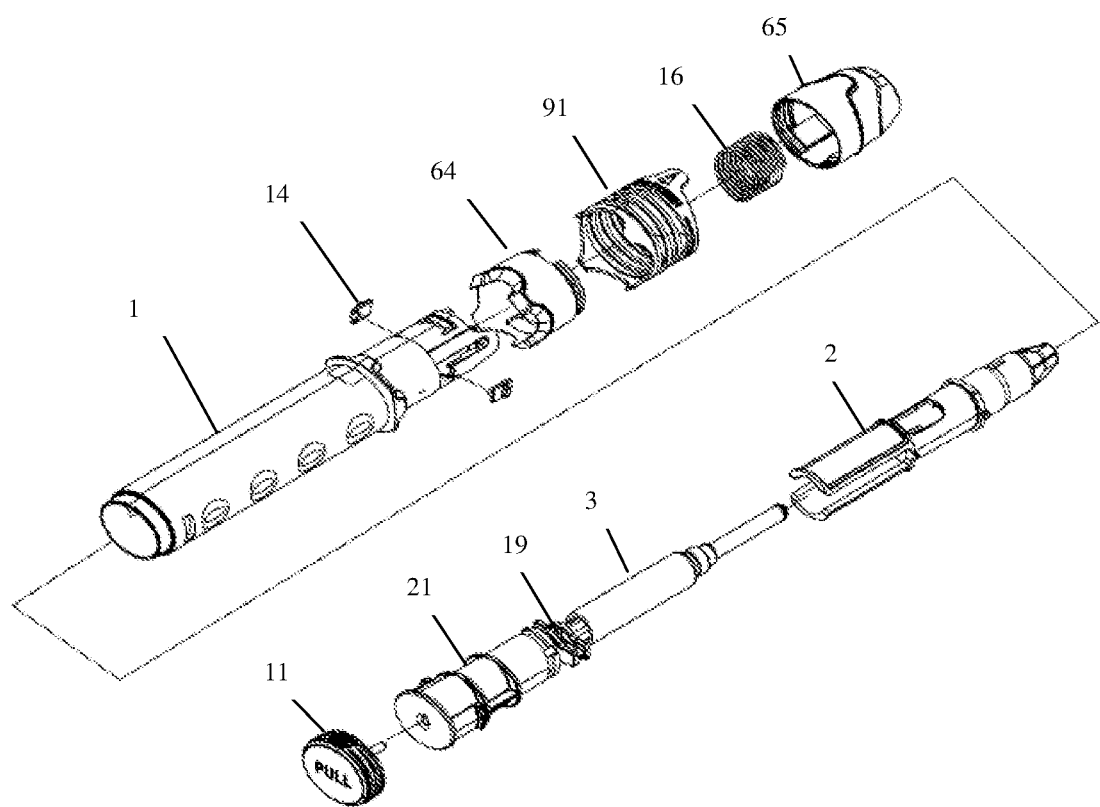
FIG. 16 is an exploded view of yet another embodiment of an autoinjector.
Figure 17:
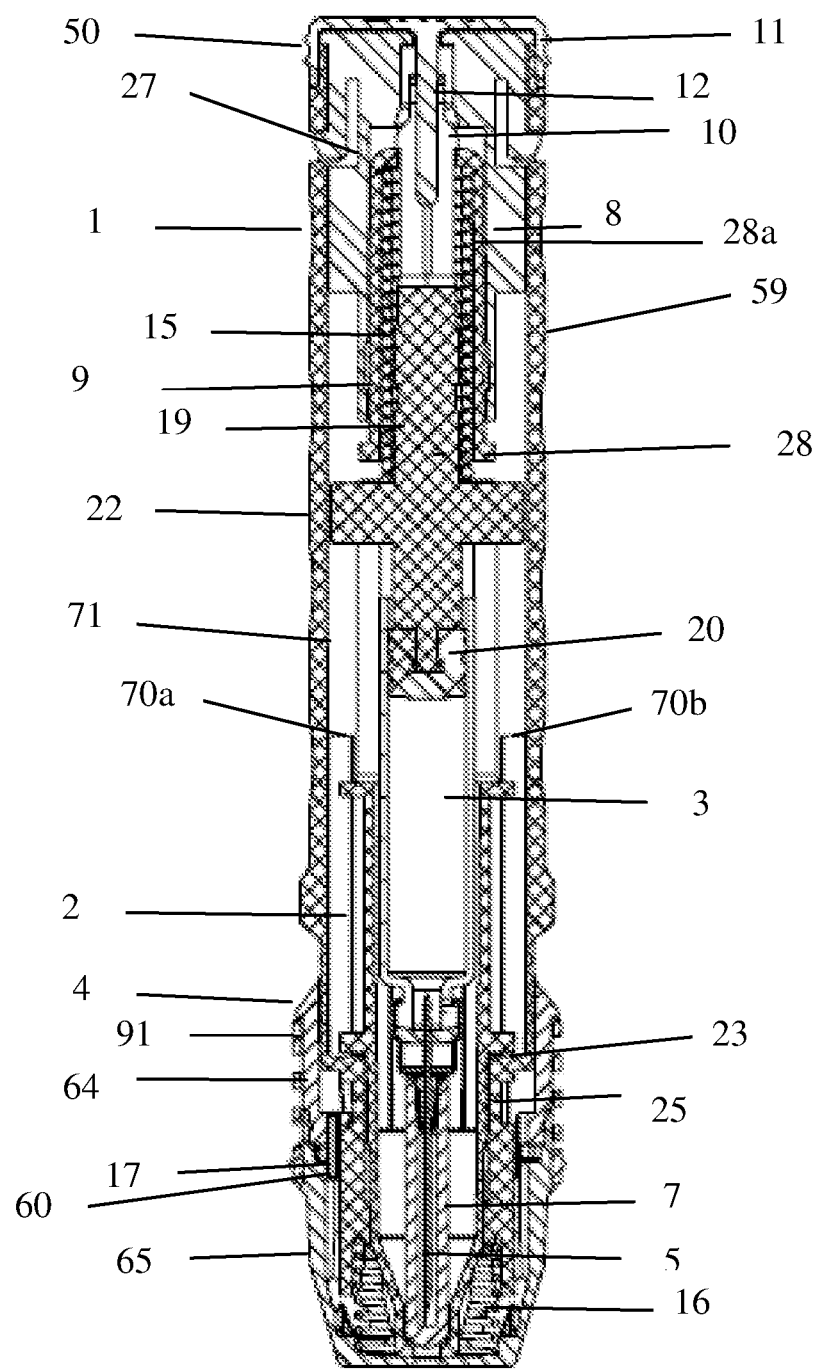
FIG. 17 is a longitudinal view and bottom view of yet another embodiment of an autoinjector wherein sleeve 91 is provided over needle cover in the first locking position with structural details in a cross sectional view.
Figure 17:
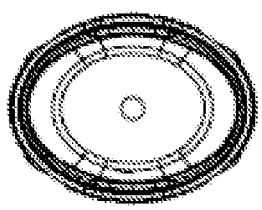

Yet another embodiment of an autoinjector 59 may be described with reference to FIG. 16 to FIG. 24. Certain features may reference the same or similar features in FIG. 4, FIG. 5, FIG. 7, and FIG. 8. FIG. 4 shows perspective view of a housing 1; FIG. 5 shows perspective view of a cartridge holder 2; FIG. 7 shows schematic view of a cam profile on the housing 1; FIG. 8 shows a perspective view of plunger 19; FIG. 16 shows an exploded view of autoinjector 59; and FIG. 17 shows longitudinal and bottom view in cross section of the autoinjector 59. Referring FIG. 8, FIG. 16 and FIG. 17, the autoinjector comprises a housing 1, a cartridge holder 2, a top cover 21, a safety cap 11, a collet 9, a first biasing member 15 associated with cartridge movement and medicament administration, a second biasing member 16 associated with needle cover locking mechanism 60 during the operation and medicament administration, needle cover 4 comprising a needle cover top 64, a needle cover bottom 65, a plunger 19 provided with two oppositely located wings 68, 68a towards the distal portion on its outer surface, a cartridge 3 and a needle sheath 7 over the needle 5. The needle cover 4 further comprises a sleeve 91.

The autoinjector 59 further comprising a sleeve 91 received on the outer surface of the needle cover 4. In an embodiment, the sleeve 91 may comprise a plastic material including thermosetting epoxy, polyimide, polyether ether ketone polyester resins, combinations thereof, and/or the like. The sleeve 91 has an internal surface and an external surface and may be made from or coating with suitable materials that provide low-coefficient of friction on the inner and external surface. The sleeve 91 has a proximal end 94 and a distal end 95, wherein the proximal and distal ends 94, 95 are separated by coil body 96 extending along a coiled axis. The coil body 96 may comprises a fibre-reinforced polymer material being substantially wound in one direction only helically and concentrically at prescribed winding angle.

The sleeve 91 is coextensive with the needle cover 4, wherein the proximal end 94 is positioned around the needle cover top 64 and the distal end 95 is positioned around needle cover bottom 65. The sleeve 91 has internal surface relative to which the outer bearing surface of needle cover top 64 is freely slidable. For example, when the needle cover 4 is moved backwards towards the proximal end upon the actuation of autoinjector 59, the sleeve 91 may remain stationary by allowing the needle cover 4 to slide therein As described herein, the autoinjector 59 should be grasped proximal to the needle cover 4. The sleeve 91 has an external surface against which the user's hand may be positioned accidentally and may hold the needle cover 4 and sleeve 91 during actuation of the autoinjector 59. The sleeve 91 may be in stationary position relative to the user grasping, since the internal surface of the sleeve 91 has low-coefficient of friction that has slidable fit with the needle cover 4 which allows the backward movement of the needle cover 4 toward distal end without any obstruction.

The coil body 96 acts as a helical spring and caused the compression of the sleeve 91 when the proximal end 94 and the distal end 95 of the sleeve 91 are urged toward each other when the needle cover 4 may slidably move towards proximal end. As the needle cover 4 moves backward, the sleeve 91 get compressed by the coil body 96 and maintain the sleeve 91 in constant contact with the needle cover 4.

Some of the embodiments of an autoinjector 59 comprise a driver assembly 8; a first biasing member 15; a second biasing member 16; a safety cap 11; and a top cover 21; the first biasing member 15 configured to bias the driver assembly 8; the drive assembly 8 comprises a collet 9 and a collapsible lock 10

Needle cover locking mechanism 60 may be described by referring to FIG. 17, FIG. 18A, FIG. 18B and FIG. 18C that disclose an autoinjector 59 for a medicament administration that comprises: a housing 1 having a proximal portion and a distal portion, said proximal portion of housing 1 is having a first sleeve section 22, a first shoulder 23 at the distal end of the first sleeve section 22, a second sleeve section 25 extends distally from the first shoulder 23 towards the distal portion of housing 1; a cartridge holder 2 is received within the housing 1; the cartridge holder 2 is having a proximal end and a distal end; the cartridge holder 2 is having an opening at the distal end; a cartridge 3; a plunger 19; a needle 5 fixed to the distal end of the cartridge 3; a needle cover 4, wherein the housing 1 is at least partially received within the needle cover 4; the needle cover further comprises a sleeve 91; the autoinjector further comprises a needle cover locking mechanism 60 having a first locking position and a second locking position; and the needle cover locking mechanism 60 comprises a cam profile 13, a cam follower 14; the cam follower 14 of locking mechanism 60 is located between the needle cover 4 and the second sleeve section 25 of the housing 1 in both first locking position 17 and second locking position 18.

The cam profile 13 may be provided on the outer surface of second sleeve section 25 on the distal portion of the housing 1. Some of the examples of autoinjector 59, comprising a pair of diametrically opposite cam profiles 13a, 13b on the distal portion of the housing 1. A pair of cam followers 14a, 14b received on the corresponding cam profiles 13a, 13b and positioned between the needle cover 4 and the housing 1.

Figures 18A, 18B, 18C:
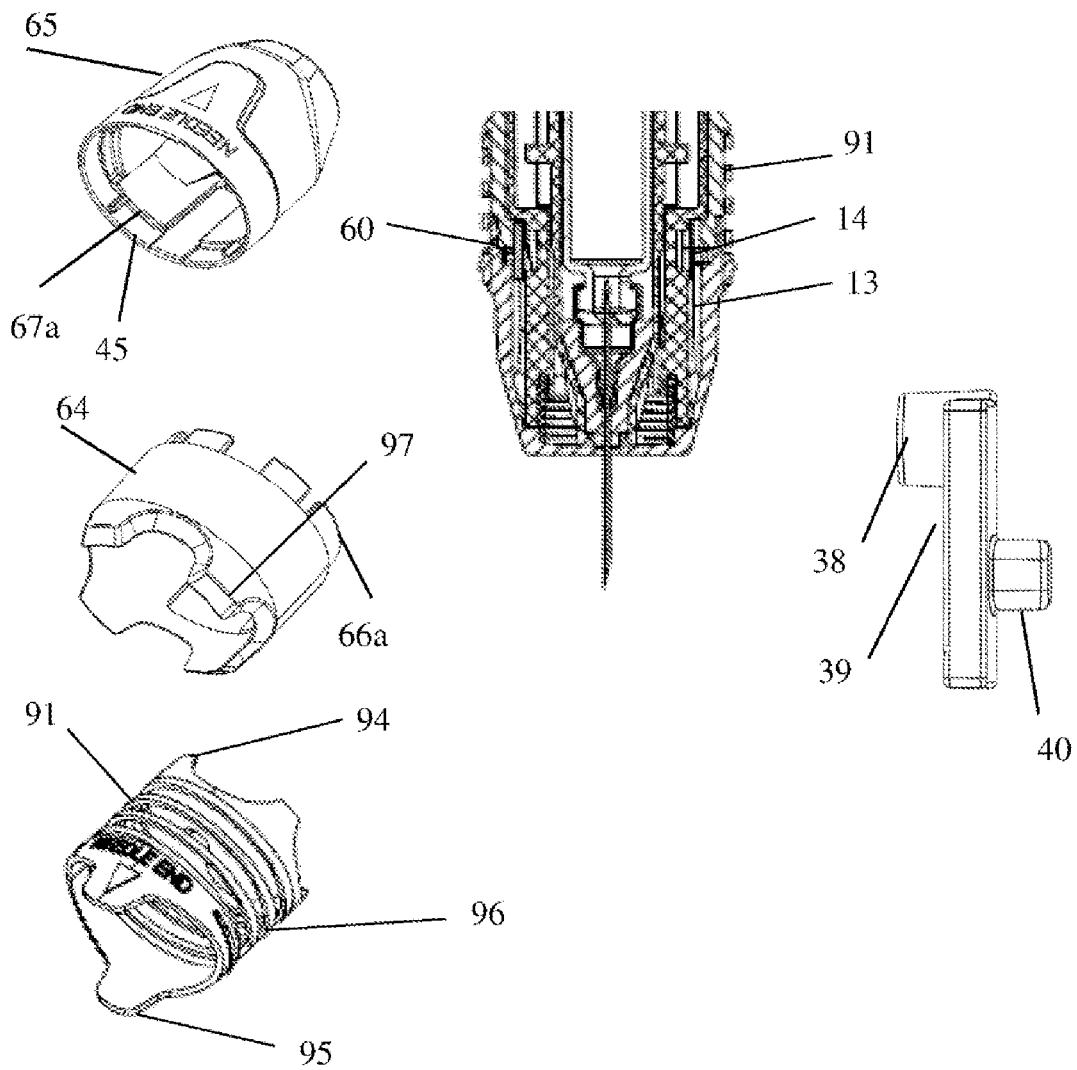
FIG. 18A shows a perspective view of needle cover top, needle cover bottom and a Sleeve 91 of yet another embodiment of an autoinjector.
FIG. 18B shows front view of a cam follower of yet another embodiment of an autoinjector same as shown in FIG. 3B.
FIG. 18C shows cross-sectional view of position of a cam follower on the second sleeve section of the housing after actuation and before needle cover extension with a sleeve 91 over a needle cover of yet another embodiment of an autoinjector.

The autoinjector 59 for a medicament administration comprises a needle cover locking mechanism 60. FIG. 18A shows perspective view of a needle cover top 64, a needle cover bottom 65 and a sleeve 91; FIG. 18B shows front view of cam follower 14; FIG. 18C shows sectional view of position of the cam follower 14 on the second sleeve section 25 of the housing 1 after actuation and before needle cover extension; Referring to FIG. 18B and FIG. 18C, the needle cover 4 of the locking mechanism 60 may comprise a cam profile 13 on outside surface of the second sleeve section 25 and a cam follower 14. The cam follower 14 of the locking mechanism 60 may be located between the needle cover 4 and the second sleeve section 25 of the housing 1 in both the first locking position 17 and the second locking position 18. The needle cover 4 may be of cylindrical, oval or elliptical shape. The needle cover 4 may comprise a proximal portion needle cover top 64 and a distal portion needle cover bottom 65. There may be provided a plurality of projections 66a on the needle cover top 64 towards the distal portion. The projections 66a may be over the entire circumference. There may be stopping ridge 97 provided towards the proximal portion of the needle cover top 64. The stopping ridge 97 inhibits the sleeve 91 from extending beyond the outer periphery of needle cover top 64. There may be ribs 67a provided over the inner surface of the needle cover bottom 65 towards the proximal portion. The circumferential diameter of the outer surface of the plurality of projections 66a can be slightly smaller than the circumferential diameter of the inner surface of the proximal portion of the needle cover bottom 65 as to make a firm snap fit between the needle cover top 64 and needle cover bottom 65. Further the distal end of the plurality of projections 66a abut the proximal end of the ribs 67a to get snapped up the needle cover top 64 and needle cover bottom 65. Additionally, the needle cover top 64 and needle cover bottom 65 may be ultrasonically welded. There may be a needle cover groove 45 that runs on the inner surfaces of both needle cover top 64 and needle cover bottom 65 and positioned in an aligned manner. The purpose of the needle cover groove 45 may be to provide a path for the cam follower protrusion 40 of the cam follower 14 to traverse both during the actuation and medicament administration. The sleeve 91 may be observed to be surrounding the outer surface of the needle cover 4.

The details of a housing 1, a cartridge holder 2, cam profile 13 on the housing 1 and a Plunger 19 in the embodiment of autoinjector 59 referred in FIG. 16 to FIG. 24 are may be the same or similar as described in earlier paragraphs with reference to FIG. 4, FIG. 5, FIG. 7 and FIG. 8 in the embodiment of autoinjector 59 referred in FIG. 1 to FIG. 13.

There may be plurality of inward transverse projections extending from the inner surface 71 of the housing 1 towards the distal portion. Referring to FIG. 17, in the preferred embodiment the first sleeve section 22 of the housing 1 may be having an inward transverse projections 70b, 70a extending from the inner surface 71 of the housing. The inward transverse projections 70b, 70a may be provided in diametrically opposite directions. The inward transverse projections 70b, 70a may be rectangular in shape. As referred in aforementioned embodiments of FIGS. 1-13, the plunger 19 provided with two oppositely located wings 68,68a. The wings 68,68a of plunger 19 engaged with the inward transverse projection 70a,70b of housing 1, the plunger 19 is prevented from hitting the cartridge 3 surface and no stress occurs on the cartridge 3.

Some examples of autoinjector 59 disclose wherein the distal closed end of the cartridge holder 2 abuts the inside surface of needle cover 4 in the first locking position 17 as shown in FIG. 17. The second biasing member 16 received over the distal closed end of the cartridge holder 2 and held between the housing 1 and the needle cover 4. The needle cover 4 is biased by the second biasing member 16 from the housing 1.

Figure 19:
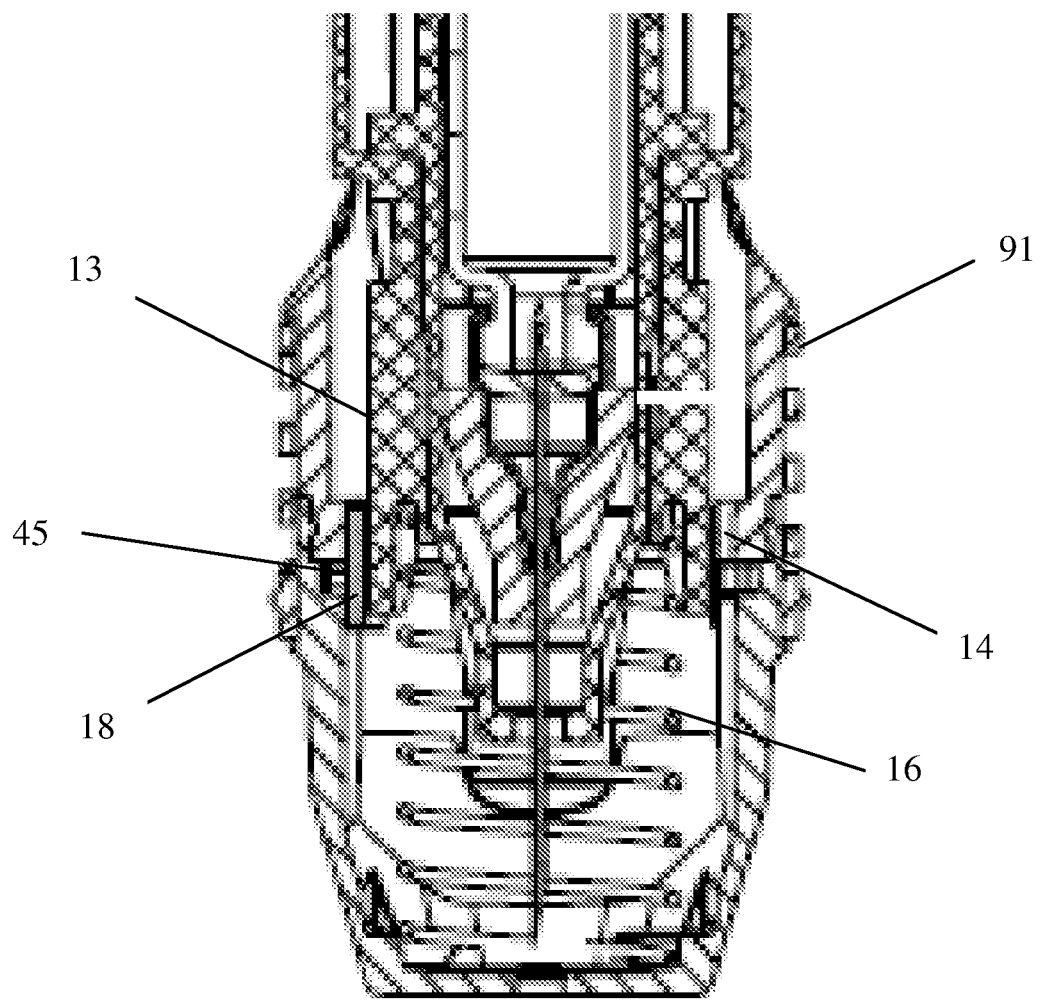
FIG. 19 shows the position of the cam follower on the housing of an auto injector after needle cover extension of yet another embodiment of an auto injector wherein a sleeve 91 is provided over a needle cover.

FIG. 19 shows the position of the needle cover 4 in the second locking position 18. In the second locking position 18, the cam follower button 38 of the cam follower nut 14 mates with cylindrical contour surface 48a of the cam profile 13.

Referring to FIG. 7 and FIG. 18B the cam profile 13 provided on the outer surface of second sleeve section 25 on the distal portion of the housing 1 may be described as follows. An angled contour surface 41 of the cam profile 13 may have a frustum of a cone contour surface 42 in the proximal portion and cylindrical or rectangular contour surface 42a towards the distal portion. Cam profile 13 may be formed out as a groove 43 in the housing to facilitate engagement or coupling of cam follower button 38, on to housing 1. The cam profile 13 may be formed out as a protrusion on the housing 1 to facilitate engagement or interaction of cam follower button 38, on to housing 1. The engagement or interaction may be by snap fit, a butt joint, a bayonet coupling, welding or other methods of attachment.

Figure 20:
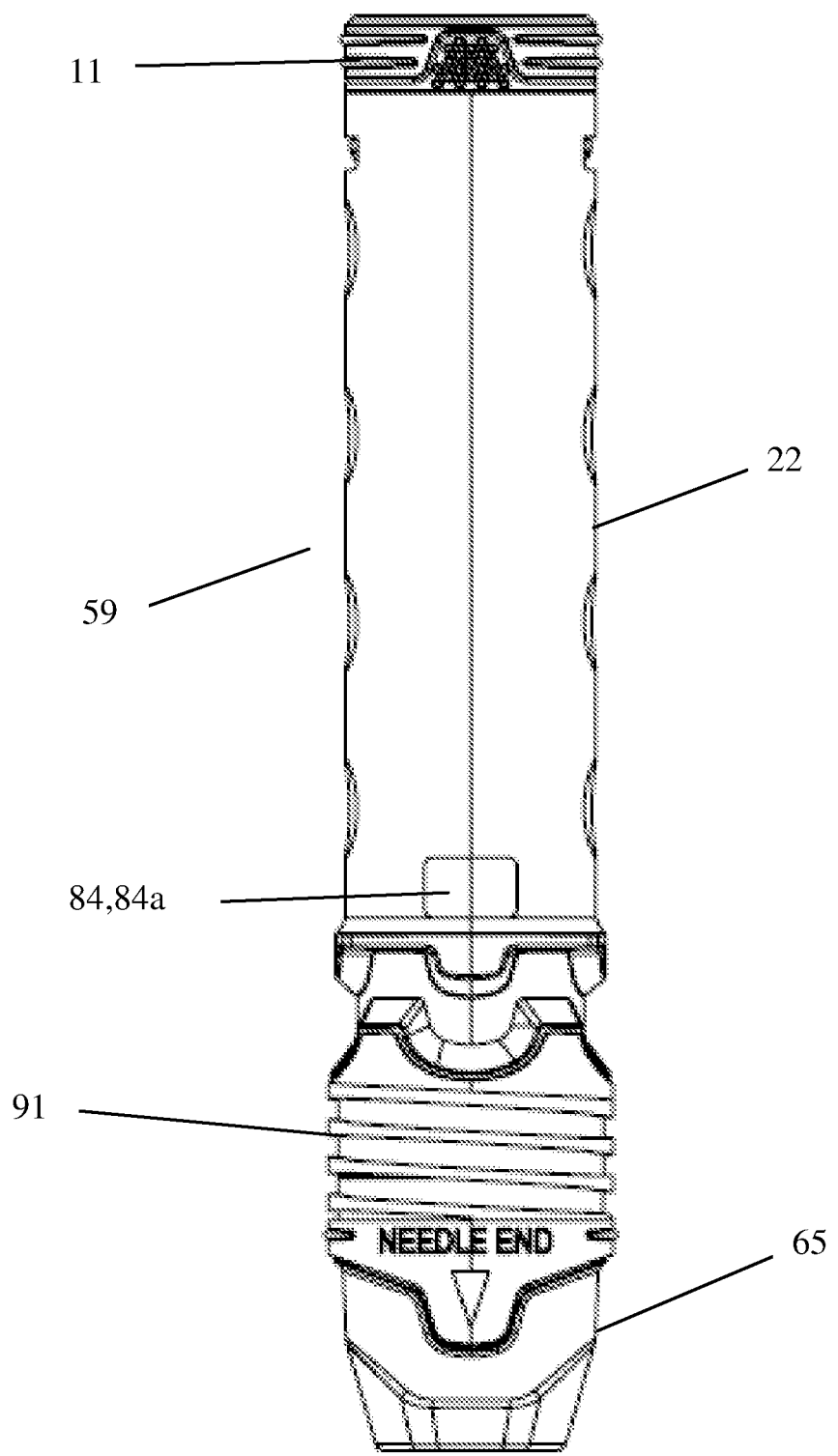
FIG. 20 shows a front view of yet another embodiment of an autoinjector with safety cap in place wherein a sleeve 91 is provided over needle cover.

FIG. 20 shows a front view of an autoinjector 59 with safety cap 11 in place. The windows 84,84a permit the user to view the contents of the cartridge. In some of the embodiments, windows 84, 84a may be provided on the outer surface of the first sleeve section 22 of the housing 1. Window 84a may be located in a diametrically opposite position to window 84. In some of the embodiments, windows 84, 84a may be provided on the outer surface of the first sleeve section 22 towards the distal portion of the housing 1.

An autoinjector 59 for administering a fluid medicament to a subject comprising: a housing 1 having a proximal portion and a distal portion, a cartridge holder 2 received within the housing 1, the cartridge holder 2 is having a proximal end and a distal end; an opening at the distal end; a cartridge 3; the housing 1 is having a first sleeve section 22; first sleeve section 22 is having inward transverse projections 70b, 70a on the inner surface 71; a plunger 19; the plunger 19 is having two wings 68, 68a provided on the outer surface; a needle cover 4, wherein the housing 1 is at least partially received within the needle cover 4; the needle cover further comprises a sleeve 91; the auto injector 59 further comprises a needle cover locking mechanism 60 having a first locking position 17 and a second locking position 18; wherein the needle cover locking mechanism 60 comprises a cam profile 13; and a cam follower 14; wherein the cam follower 14 of locking mechanism 60 is located between the needle cover 4 and the second sleeve section 25 of the housing 1 in both first locking position 17 and second locking position 18; wherein the distal surfaces 80, 80a of the wings 68, 68a of the plunger 19 engage the surface of the inward transverse stopping projection 70b, 70a of the housing 1 at the end of the medicament administration.

The working of the autoinjector 59 may further be illustrated referring to FIG. 5, FIG. 8, FIG. 17 and FIG. 20 to FIG. 24. In the initial position the safety cap 11 may be in the proximal end of the autoinjector 59 mounted over the housing 1 as shown in FIG. 20. In this initial position the medicament may be visible through the windows 84, 84a on the outer surface of the housing 1 and due to the openings 77, 77a on the cartridge holder 2. The windows 84, 84a on the outer surface of the housing 1 may be formed by virtue of the unwrapped label over the transparent housing 1 portion corresponding to the shape of window. The transparent windows 84, 84a and the openings 77, 77a may be in an alignment. The purpose of the window 84, 84a may be to ensure visibility of stopper 20 on completion of medicament administration. The safety pin 12 of the safety cap 11 may pass through the top cover 21 central aperture 52. The positioning of the safety pin 12 inside the central aperture 52 may prevent the collapsible lock portion 86, 86a of the plunger 19 access to the frusto conical cam surface 58 of the top cover 21. Further collapsible lock portion 86, 86a of the plunger 19 may be locked with the collet 9 by the first biasing member 15. This can help the autoinjector 59 to be on a non-activated position. Further insertion of safety cap 11 through the collapsible snap lock 10 may prevent accidental unlocking of the drive assembly 8. In the initial position, the needle cover top 64 and needle cover bottom 65 of the needle cover 4 may be biased by the second biasing member 16. The second biasing member 16 may be biased from the housing 1. The distal end of the cylindrical portion of the cartridge holder 2 may have an engagement with the proximal end of the inner surface of the cover bottom 65. The engagement may be a simple butt joint. However, the proximal end 29 of the cartridge holder 2 does not have any engagement with the collet 9. The collet 9 comprises cylindrical section 28a from proximal end to distal end and a distal flange 28. There may be a gap between the proximal end of the cartridge holder 2 and the collet 9 as shown in FIG. 2.

Figure 21:
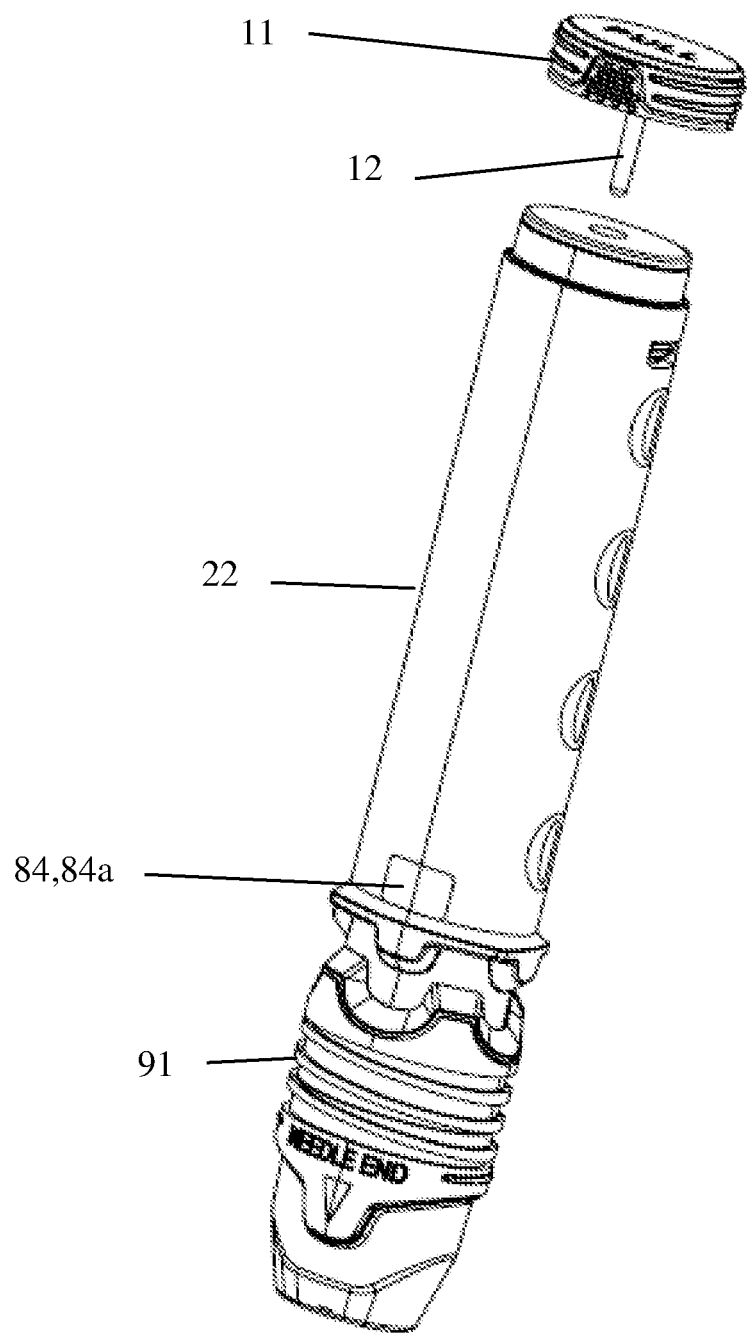
FIG. 21 shows a perspective view of yet another embodiment of an autoinjector with safety cap removed wherein a sleeve 91 is provided over a needle cover.

FIG. 21 shows a perspective view of the autoinjector 59 with safety cap 11 removal, for example by holding the ridges of the safety cap 11 and pulling proximally. This action may place the autoinjector 59 in an activating position as a result of collapsible lock portion 86, 86a of the plunger 19 (Shown in FIG. 8) finding access to the frusto conical cam surface 58 (shown in FIG. 23) of the top cover 21. The sleeve 91 is at least partially around the outer surface of the needle cover 4.

Figure 22:
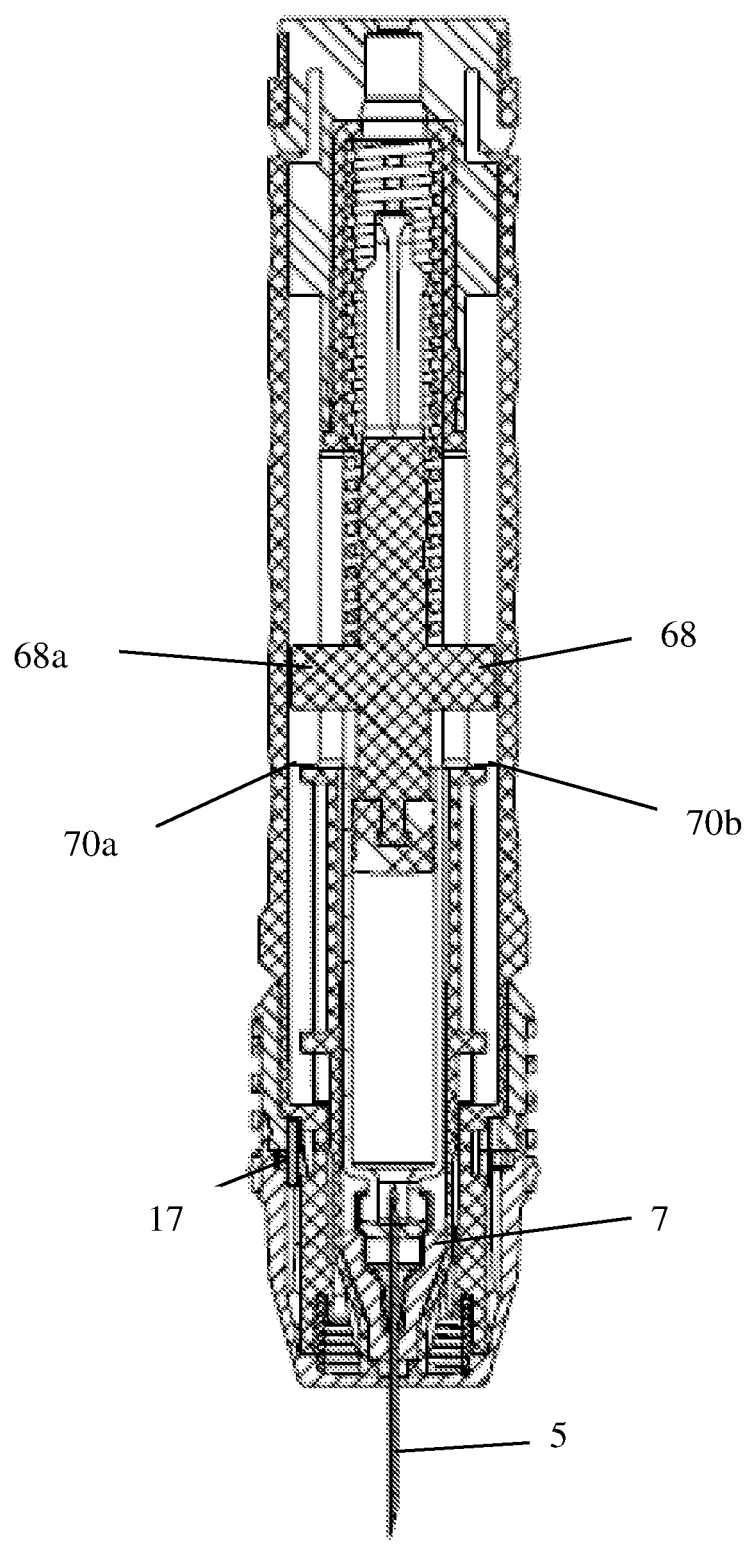
FIG. 22 shows a sectional view of yet another embodiment of an autoinjector with needle exposed from the needle cover bottom before medicament administration wherein a sleeve 91 is provided over a needle cover.

FIG. 22 shows a sectional view of the autoinjector 59 with needle 5 exposed from the needle cover bottom 65 of the needle cover 4 before the medicament administration. After the safety cap 11 is removed the user may hold the autoinjector 59 first sleeve section 22 of the housing 1 in the hand and press the needle cover bottom 65 on to the body for actuation. The needle cover bottom 65 and needle cover top 64 of the needle cover 4 may move in the proximal direction towards the housing 1 and may push the cartridge holder 2 backward due to the butt joint between the needle cover bottom 65 and the cartridge holder 2 and butt against the collet 9. The cartridge holder 2 may push back the collet 9 due to the butt joint between the needle cover 4 and the cartridge holder 2 which in turn may push the collapsible lock portion 86, 86a to release the first biasing member 15. The first biasing member 15 and the second biasing member 16 may be spring. The collapsible lock portion 86, 86a may move inward through the chamfer provided on the top cover 21 resulting in unlocking of the collet 9 of the drive assembly 8 and collapsible lock 10 of the plunger 19. The first biasing member 15 may relax and hold the collet 9 against the top cover 21 at the proximal end and may push the cartridge 3 along with the needle on the distal end. As a consequence the needle 5 may get enough force from the first biasing member 15 to pierce the needle sheath 7, clothing of the patient and finally though the skin. While the needle cover bottom 65 and the needle cover top 64 may be pushed against the housing 1, the cam follower 14 may move along the cam profile angled contour surface 41 and may occupy the proximal position. The cam follower 14 may have both rotational and linear movement with respect to the needle cover bottom 65 and needle cover top 64 of the needle cover 4 along while the needle cover 4 may have only linear motion along with the sleeve 91. The sleeve 91 is at least partially around the outer surface of the needle cover 4.

The sleeve 91 has an external surface against which the user's hand may be positioned accidentally and may hold the needle cover 4 and sleeve 91 during actuation of the autoinjector 59. The sleeve 91 may be in stationary position relative to the user grasping, since the internal surface of the sleeve 91 has low-coefficient of friction that has slidable fit with the needle cover 4 which allows the backward movement of the needle cover 4 toward distal end without any obstruction.

As the needle cover 4 moves backward, the sleeve 91 get compressed by the coil body 96 and maintain the sleeve 91 in constant contact with the needle cover 4.

After removing the needle cover 4 from the body, the needle cover 4 is extended forward towards distal end by the action of spring. As the needle cover 4 extended forwards, the sleeve 91 is slipping from the user's hand and traverse with the needle cover 4.

During forward movement of the needle cover 4, the sleeve 91 remains stationary relative to the outer bearing surface of needle cover 4.

The needle sheath 7 is positioned over the needle 7 such that the open end of the sheath fits over and around the needle 5. The length of the sheath 7 is such that its closed end is slightly beyond or spaced from the end of needle 5. The cartridge 3 moves forward whereby the needle sheath 7 is compressed the most between the cartridge holder 2 and the cartridge 3. At this juncture, the cartridge 3 may move forward and the distal surface of the cartridge 3 may have an engagement with the proximal surface of the compressed needle sheath 7.

Some of the examples of autoinjector 59 disclose wherein the proximal end of the cartridge holder 2 abuts the distal end of the collet 9 on actuation of the autoinjector 59 by pressing the needle cover 4 against the body after the removal of the safety cap 12 due to backward movement of the cartridge holder 2.

Some of examples of an autoinjector 59 disclose wherein the top cover 21 inner surface is having a chamfer shape; the collapsible lock 10 is having a collapsible lock portion 86, 86a towards the proximal end; the collapsible lock portion 86, 86a moves inward through the chamfer on actuation of the autoinjector 59 by pressing the needle cover 4 against the body after the removal of the safety cap 12 due to backward movement of the cartridge holder 2 resulting in unlocking of the collet 9 and collapsible lock 10 of the plunger 19. FIG. 2, FIG. 8 and FIG. 22 may be referred for details.

Figure 23:
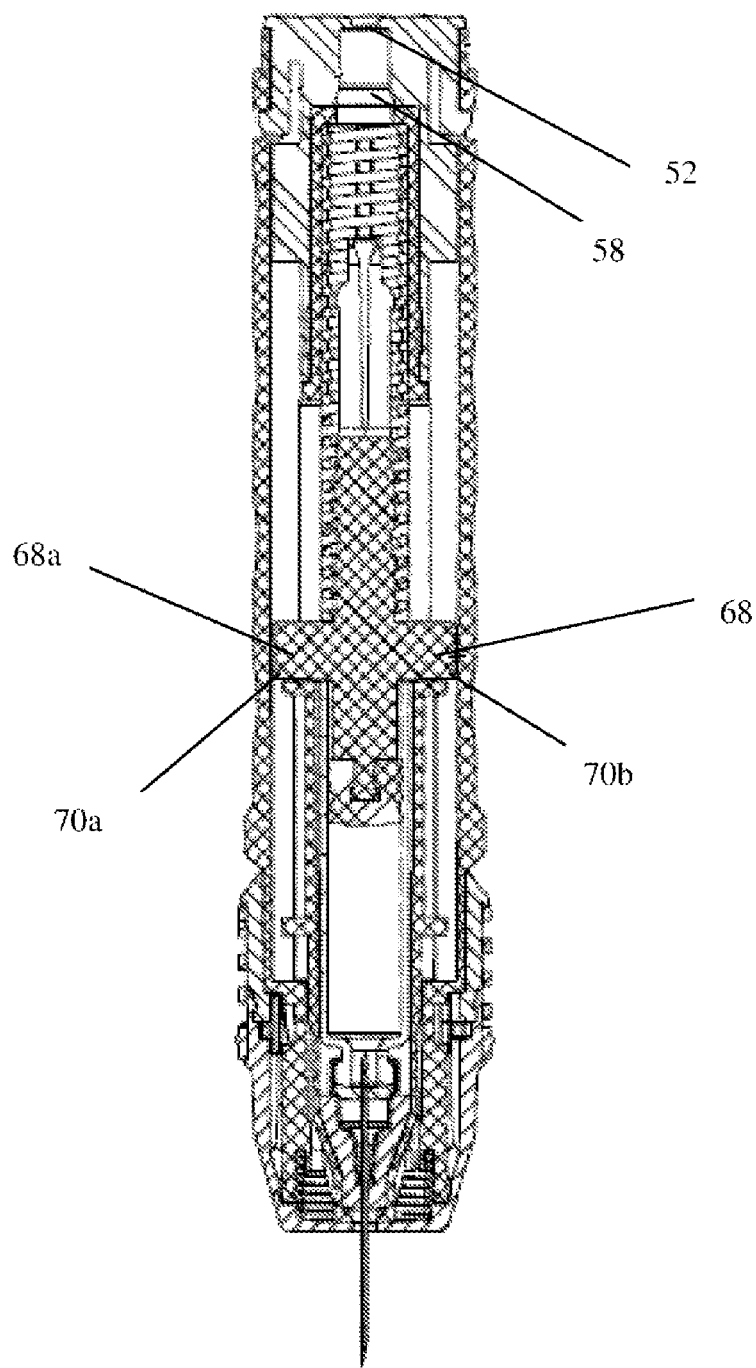
FIG. 23 shows a sectional view of yet another embodiment of an autoinjector with needle exposed from the needle cover bottom after medicament administration wherein a 91 sleeve is provided over a needle cover.

FIG. 23 shows a sectional view of the auto injector 59 with needle 5 exposed from the needle cover bottom 65 after medicament administration. Once the needle 5 may be pierced into the skin of the patient, due to the spring force of the first biasing member 15 the plunger 19 may move forward and may deliver the pre-defined volume of medicament through the needle 5. The plunger 19 may move from the position with respect to the housing 1 as shown in FIG. 22 and the distal surface 80 of the left wing 68 of the plunger 19 and distal surface 80a of the right wing 68a of the plunger 19 may engage the proximal surface of the inward transverse projections 70b, 70a of the first sleeve section 22 of the housing 1 thus preventing the plunger 19 from hitting the cartridge 3 surface, inducing no stress on the cartridge 3. During this stage the stopper 20 may move toward the distal end and the stopper 20 position may correspond with the window 84, 84a provided on the distal portion of the first sleeve section 22 of the housing 1 and thus providing a visual indication for the user that the medicament is delivered. The sleeve 91 may be observed to be surrounding the outer surface of the needle cover 4.

Some of the examples of an autoinjector disclose wherein the distal surfaces 80, 80a of the left wing 68 and right wing 68a of the plunger 19 engage the surface of the inward transverse projection 70b, 70a of the housing 1 at the end of the medicament administration; contacting surfaces 82, 83 of wing 68 engage with the surfaces of the slots 76c, 76b of the cartridge holder 2; and contacting surfaces 82a, 83a of wing 68a engage with the surfaces of the slots 76e, 76d of the cartridge holder 2. FIG. 8 and FIG. 23 may be referred for details.

Figure 24:
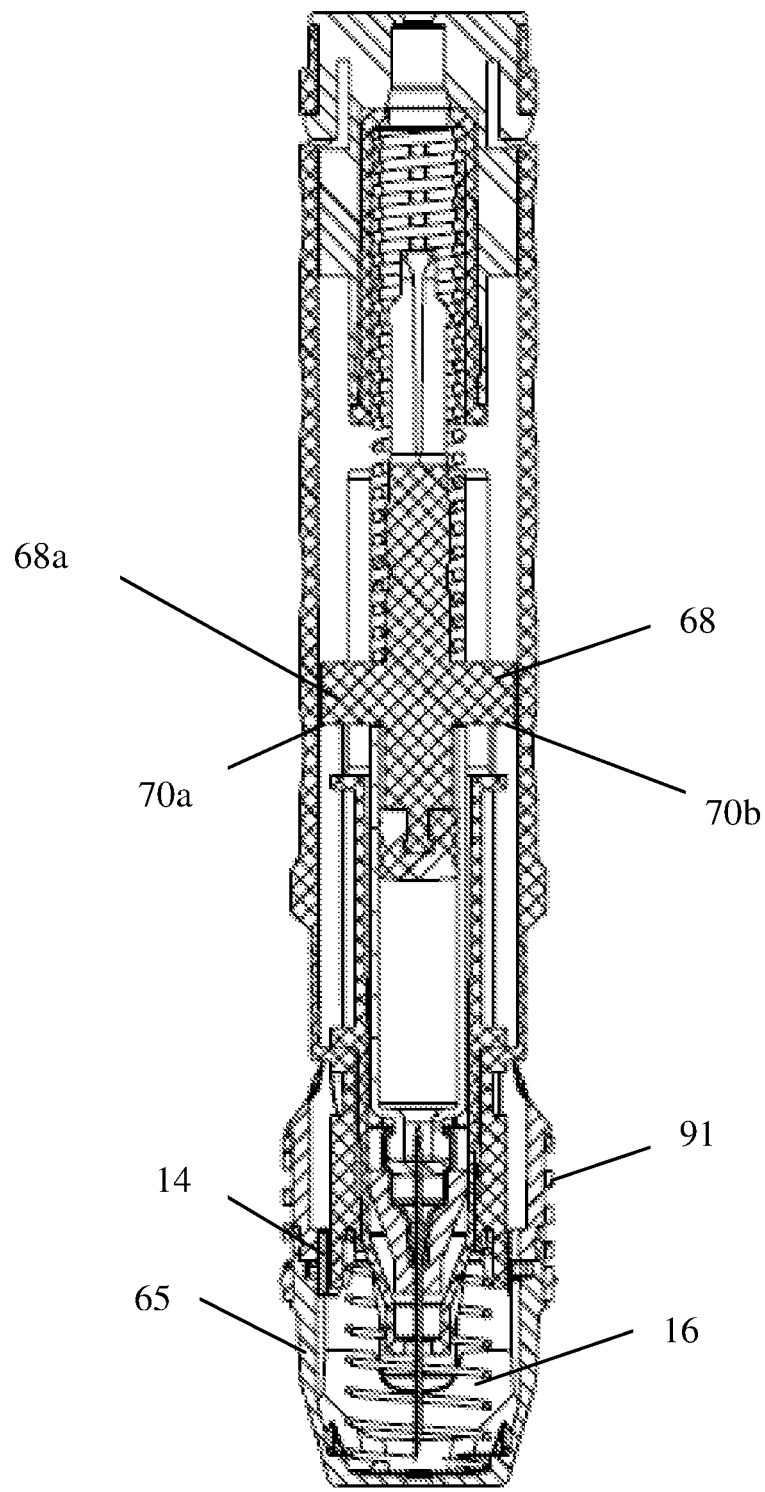
FIG. 24 shows a sectional view of yet another embodiment of an autoinjector with needle cover top, needle cover bottom in extended position protecting the exposed needle after medicament administration wherein a 91 sleeve is provided over a needle cover.

FIG. 24 shows a sectional view of the autoinjector 59 with needle cover top 64 and needle cover bottom 65 of the needle cover 4 in extended position protecting the exposed needle 5 after the medicament administration. During delivery of the medicament, the autoinjector 59 may be held against the body for the desired period as the plunger 19 travels through the autoinjector 59 before the autoinjector 59 may be withdrawn from the body. As the autoinjector 59 is withdrawn from the body, the needle cover 4 comprising needle cover top 64 and needle cover bottom 65 may extend forward due to the tension of the second biasing member 16. The cam follower 14 may follow the cylindrical contour surface 42a of the cam profile 13. Referring FIG. 7, the cylindrical contour surface 42a being longer than cam profile angled contour surface 41 the longer travel of the cam follower 14 leading to longer extension of the needle cover 4. During this stage the needle cover 4 may extend forward and may get locked with the housing 1 at the second locking position 18. There may also be a fool-proof locking of the needle cover 4 with housing 1 such that both forward and backward movement of needle cover 4 may be restricted. The sleeve 91 may be observed to be surrounding the outer surface of the needle cover 4.

The cam profile 13 may be provided on the outer surface of second sleeve section 25 on the distal portion of the housing 1. An angled contour 41 of Cam profile 13 may have in the proximal portion a frustum of a cone contour 42 and cylindrical contour 42a towards the distal portion. The distal portion contour surface 42a shown in FIG. 7 may be a cylindrical one. Cam profile 13 may be formed out as a groove 43 in the housing to facilitate a coupling of cam follower button 38, on to housing 1. The cam profile 13 may be formed out as a protrusion on the second sleeve section 25 of the housing 1 with a void space defining the boundaries of the protrusion to facilitate interaction of cam follower button 38 into the void space. The interaction may be by snap fit, a bayonet coupling or other methods of attachment that may facilitate free movement of the cam follower button 38. Further the protrusion 40 of the cam follower 14 may mate with groove 45 on the inner surface of the needle cover 4 both in the first locking position 17 and the second locking position 18. It may be considered that groove 45 (refer FIG. 18A and FIG. 19) on the inner surface of the needle cover 4 traverses both in the needle cover top 64 and the needle cover bottom 65. The advantage thereof may be that the protrusion 40 provided over the width of the cam follower 14 component may establish effective operable connection to the corresponding groove 45 provides better stability between the needle cover 4 and second sleeve section surface 25 of the housing 1.

Projections 88, 88a may be provided on the distal portion of the second sleeve section 25 of the housing 1. Projection corresponding to numeral 88 is shown in FIG. 7 whereas the opposite projection numeral 88a is not shown. Fool proof locking of the needle cover 4 may be achieved by the abutment of projections 88, 88a provided on the second sleeve section 25 towards the distal end with the diametrically opposite grooves 87a, 87b provided on the inner surface of the needle cover top 64 due to the force of the relaxation of the second biasing member 16.

Figures 25A, 25B, 25C:
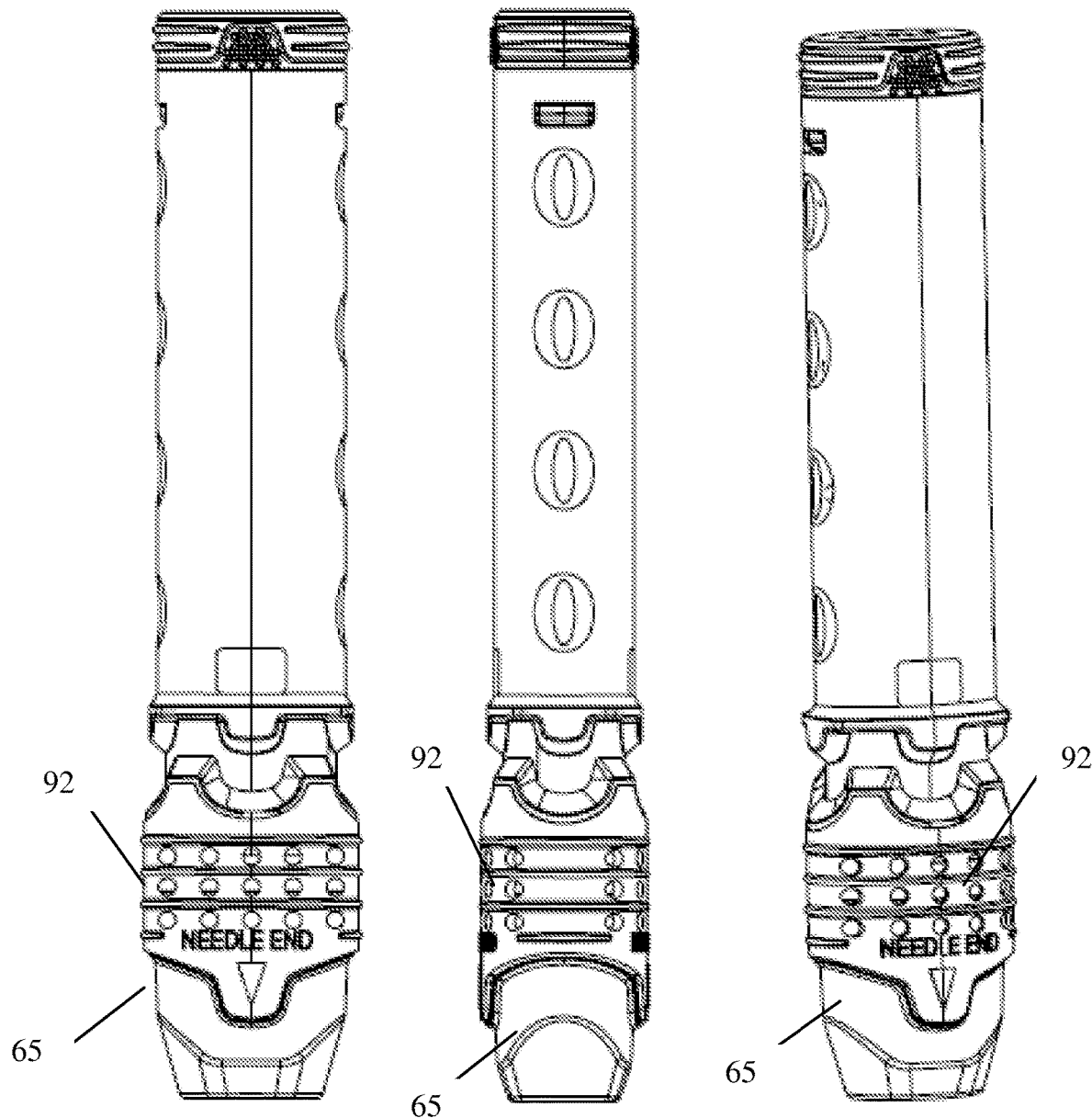
FIG. 25A shows a front view of yet another embodiment of an autoinjector wherein an sleeve 92 is provided over a needle cover and the needle cover is in the first locking/initial position.
FIG. 25C is perspective view of FIG. 25A showing an sleeve 92 provided over a needle cover and the needle cover is in the first locking/initial position.
Figure 26A:
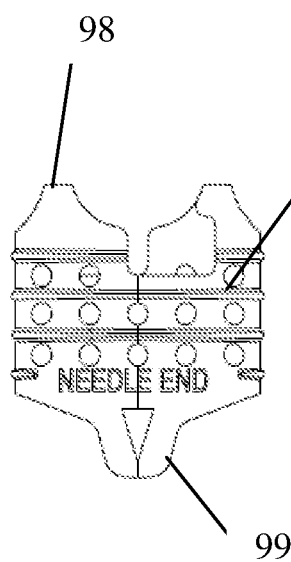
FIG. 26A is a front view of an sleeve 92.
Figure 26B:
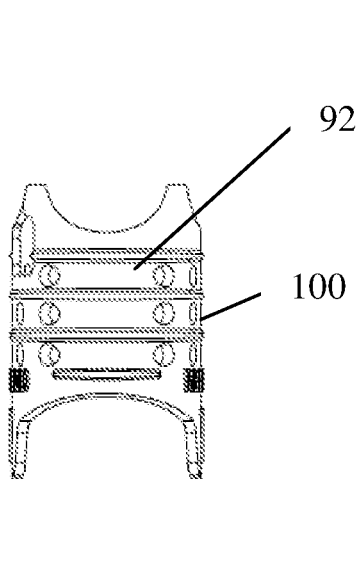
FIG. 26B is a side view of sleeve 92 of FIG. 26A.
Figure 26C:
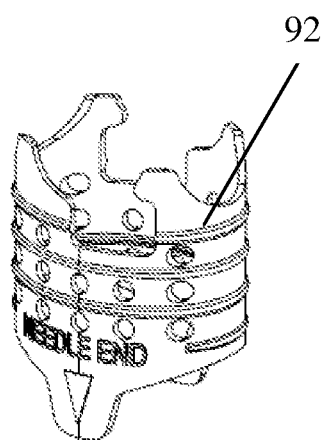
FIG. 26C is a perspective view of sleeve 92 of FIG. 26A.

Yet another embodiment of an autoinjector 59 may be described with reference to FIG. 25A, FIG. 25B, FIG. 25C and FIG. 26A, FIG. 26B and FIG. 26C. Except for differences described, this embodiment includes all the components described in the embodiment of FIG. 1 to FIG. 13 and hereby incorporated by reference in its entirety. Modifications and variations to the components are further discussed in this embodiment. FIG. 25A shows a front view of yet another embodiment of an autoinjector wherein a sleeve 92 is provided over a needle cover and the needle cover is in the first locking/initial position; FIG. 25B is a side view of FIG. 25A showing a sleeve 92 provided over a needle cover and the needle cover is in the first locking/initial position; FIG. 25C is perspective view of FIG. 25A showing a sleeve 92 provided over a needle cover and the needle cover is in the first locking/initial position; FIG. 26A is a front view of a sleeve 92; FIG. 26B is a side view of a sleeve 92 of FIG. 26A; FIG. 26C is a perspective view of a sleeve 92 of FIG. 26A;

Referring to FIG. 25A, FIG. 25B FIG. 25C and FIG. 26A, FIG. 26B and FIG. 26C, a sleeve 92 may be provided over needle cover 4 (Refer FIG. 26A). The sleeve 92 may be an elongated elastomeric sleeve. It may be considered in this embodiment a needle cover 4 further comprises a sleeve 92. The elastomeric sleeve 92 has an internal surface and an external surface and may be made from or coating with suitable materials that provide low-coefficient of friction on the inner and an external surface. The internal diameter and an internal surface of the elastomeric sleeve 92 that together provide a close but freely slidable fit with the needle cover 4. The elastomeric sleeve 92 may include a proximal end 98 and a distal end 99, wherein the proximal and distal ends (98, 99) are separated by a tubular body 100 and the proximal and distal ends may include openings. The proximal end 98 of elastomeric sleeve 92 may be positioned around needle cover top 64. There may be stopping ridge 97 provided towards the proximal portion of the needle cover top 64 (Refer FIG. 18A). The stopping ridge 97 inhibits or prevents the sleeve 92 from extending beyond the outer periphery of needle cover top 64.

The elastomeric sleeve 92 may be at least partially coextensive with the needle cover 4, wherein the proximal end 98 may be positioned around the needle cover top 64 and the distal end 99 may be positioned around the needle cover bottom 65. As described earlier, the elastomeric sleeve 92 has friction-reducing internal surface relative to which the outer surface of needle cover top 64 may be freely slidable. The needle cover 4 may move backward towards proximal end upon the actuation of autoinjector 59. The elastomeric sleeve 92 has a substantially circular or oval cross section.

The sleeve 92 may be formed of any suitable material that maintains low coefficient of static friction on both internal and external surfaces and resilient function. The desired coefficients of friction may be below 0.5, and may preferably below 0.1. The tubular body 100 may be in elastomeric nature which acts as a spring and caused the compression of sleeve 92 when the proximal end 98 and distal end 99 of sleeve 92 are urged towards each other when the needle cover 4 may slidably move towards proximal end of autoinjector. As the needle cover 4 moves backward, the sleeve 92 gets compressed by the tubular elastomeric body 100 and maintain sleeve 92 in constant contact with the needle cover 4. The sleeve 92 has an external surface against which the user's hand may be positioned accidentally grasping the needle cover top 64 during actuation of the autoinjector 59. The elastomeric sleeve 92 may be in stationary position relative to user grasping, since the internal surface of the elastomeric sleeve 92 has slidable fit with the needle cover 4 which allows the backward movement of the needle cover 4 toward proximal end without any obstruction.

After removing the needle cover 4 from the body, the needle cover 4 gets extended forward towards distal end by the action of spring 16. As the needle cover 4 extends forward, the friction reducing elastomeric sleeve 92 slips from the user's hand and traverse with the needle cover 4.

During forward movement of the needle cover 4, the elastomeric sleeve 92 may remain stationary relative to the outer surface of the needle cover 4.

An autoinjector 59 for administering a fluid medicament to a subject comprising: a housing 1 having a proximal portion and a distal portion, a cartridge holder 2 received within the housing 1, the cartridge holder 2 is having a proximal end and a distal end; an opening at the distal end; a cartridge 3; the housing 1 is having a first sleeve section 22; first sleeve section 22 is having inward transverse projections 70b, 70a on the inner surface 71; a plunger 19; the plunger 19 is having two wings 68, 68a provided on the outer surface; a needle cover 4, wherein the housing 1 is at least partially received within the needle cover 4; the needle cover further comprises a sleeve 92; the auto injector 59 further comprises a needle cover locking mechanism 60; wherein the needle cover locking mechanism 60 comprises a cam profile 13; and a cam follower 14; wherein the cam follower 14 of locking mechanism 60 is located between the needle cover 4 and the second sleeve section 25 of the housing 1 in both first locking position 17 and second locking position 18; wherein the distal surfaces 80, 80a of the wings 68, 68a of the plunger 19 engage the surface of the inward transverse stopping projection 70b, 70a of the housing 1 at the end of the medicament administration.

Some examples disclose the sleeve 92 is provided on the outer surface of the needle cover 4.

Some examples disclose the sleeve 92 comprises a proximal end 98, a distal end 99 and a tubular body 100 extending between them.

The sleeve may comprise suitable material such as thermoset elastomers, for example natural rubbers, synthetic rubbers, thermoplastic elastomers and durable synthetic plastic material. As examples of synthetic rubbers, styrene-butadiene rubber, nitrile rubber, neoprene and ethylene-propylene rubbers generally, including copolymers and terpolymers such as ethylene-propylene terpolymer, can be mentioned. Examples of thermoplastic elastomers are styrene-butadiene-styrene, styrene-isoprene-styrene and styrene-ethylene-butylene block copolymers, as well as nylon types and olefinic, polyolefinic, polyester and polyurethane types.

The synthetic rubber also includes synthetic polyisoprene, polybutadiene, butadiene-styrene copolymers, butadiene-acrylonitrile copolymers, butadiene styrene acrylonitrile copolymers, polychloroprene and similar rubber products of 1,3-diene monomers having a markedly reduced coefficient of friction.

The surface of the elastomeric or rubber article is directly treated and the surface structure thereof is modified whereby the coefficient of friction of the rubber surface is greatly reduced without alternating the essential elastic properties of the rubber article.

Suitable low friction coatings include self-lubricating materials, such as, Nylon, or any other suitable low friction material or coating.

Examples of synthetic plastics materials are polyvinyl chloride and polyethylene. A plasticiser can be added to a plastic material makes sleeve flexible, and resilient in function. Examples of plasticisers are low molecular weight phthalates, high molecular weight phthalates and speciality plasticisers such as adipates, citrates, benzoates, trimelilates and polyoxyethylene additives such as acetal copolymers, polyacetal and polyformaldehyde.

Figure 27A:
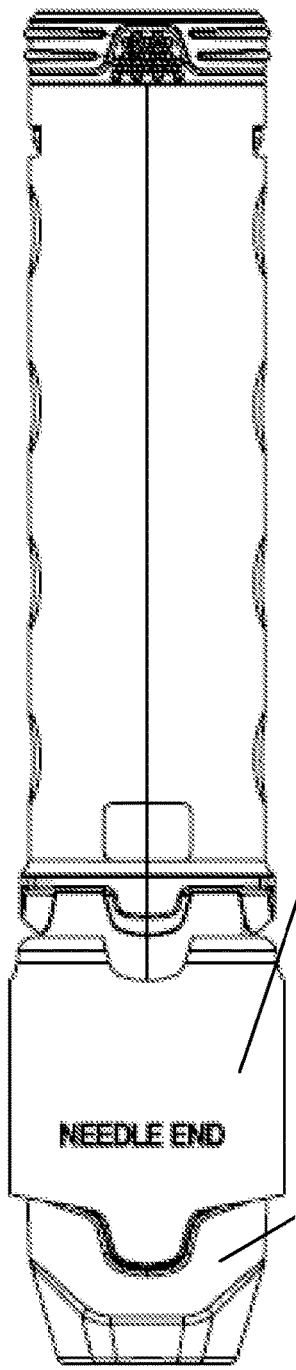
FIG. 27A shows a front view of yet another embodiment of an autoinjector wherein a sleeve 93 is provided over a housing and the sleeve 93 and needle cover are in the first locking/initial position.
Figure 27B:
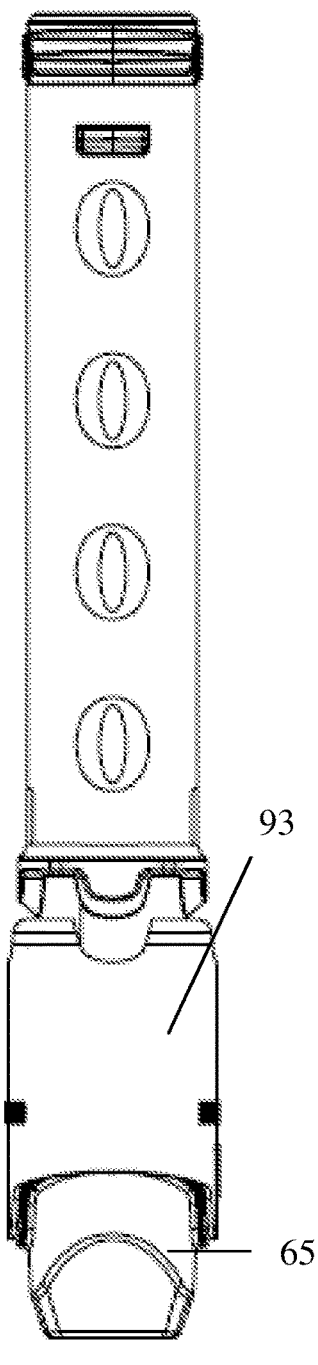
FIG. 27B is a side view of FIG. 27A showing a sleeve 93 provided over a housing and the sleeve 93 and needle cover are in the first locking/initial position.
Figure 27C:
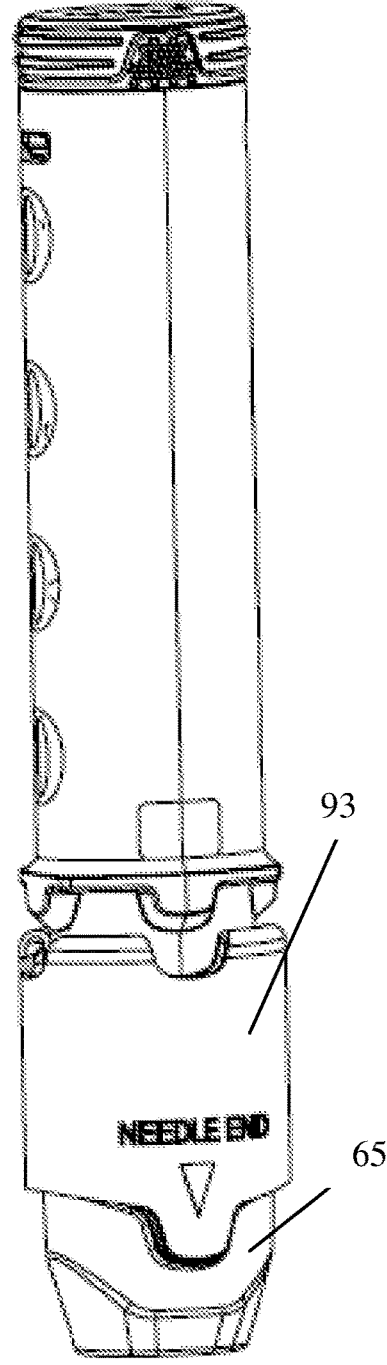
FIG. 27C is a perspective view of FIG. 27A showing a sleeve 93 provided over housing and the sleeve 93 and needle cover are in the first locking/initial position.
Figure 28A:
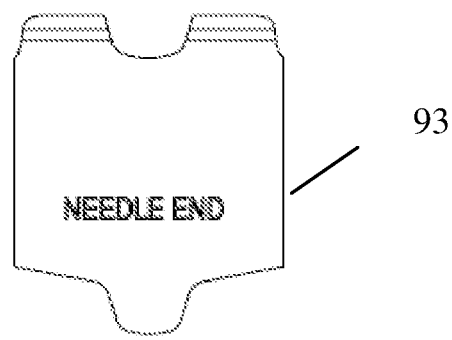
FIG. 28A is a front view of a sleeve 93.
Figure 28B:
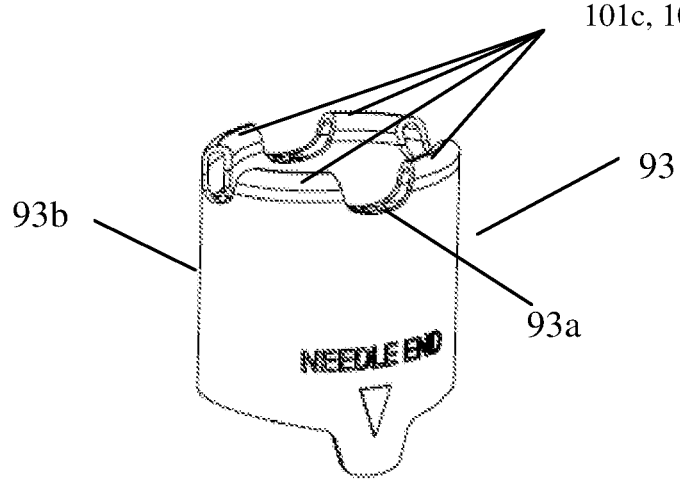
FIG. 28B is a perspective view of a sleeve 93 of FIG. 28A.
Figure 29:
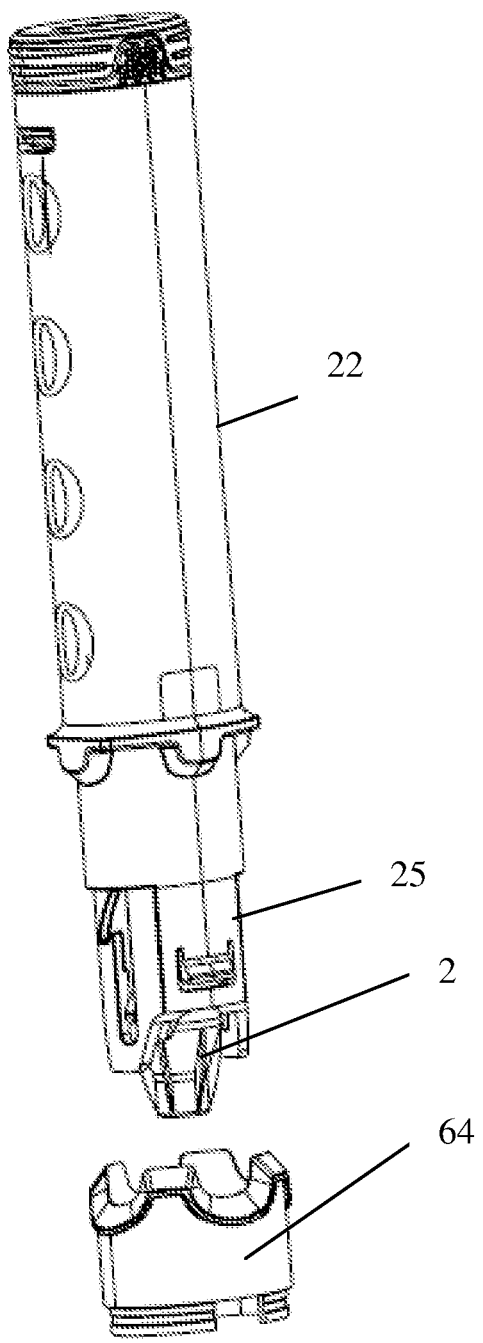
FIG. 29 shows mounting of needle cover top over a housing of an embodiment of autoinjector described with reference to FIG. 16 to FIG. 24.
Figure 30:
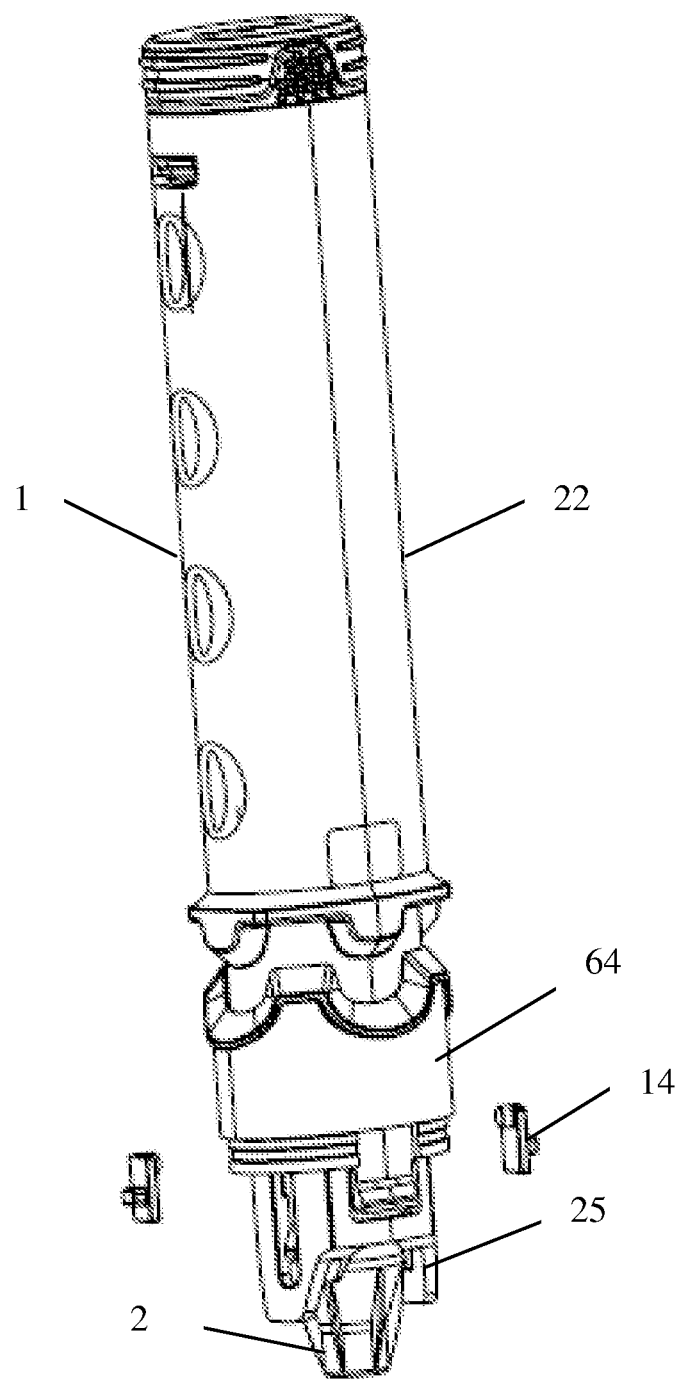
FIG. 30 shows mounting of cam followers between a housing and needle cover top of an embodiment of autoinjector described with reference to FIG. 16 to FIG. 24.
Figure 31:
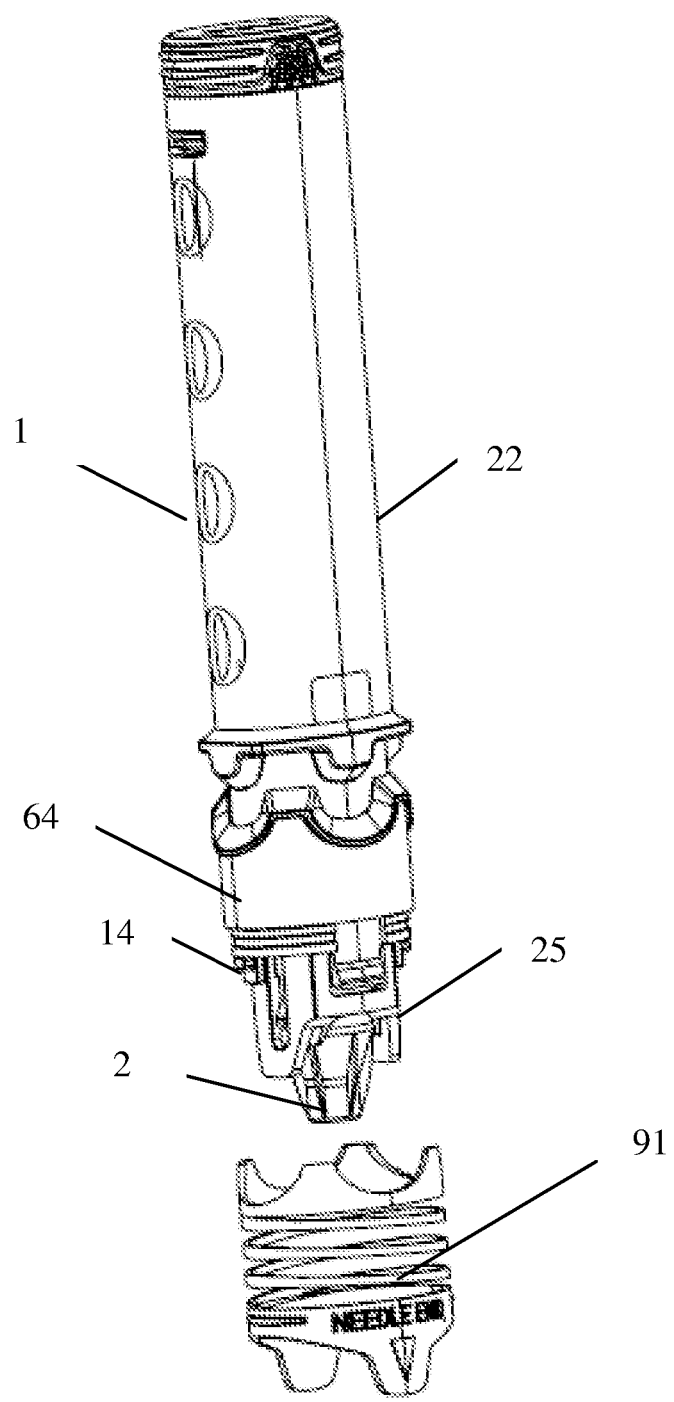
FIG. 31 shows mounting of a sleeve 91 over a needle cover top of an embodiment of autoinjector described with reference to FIG. 16 to FIG. 24.
Figure 32:
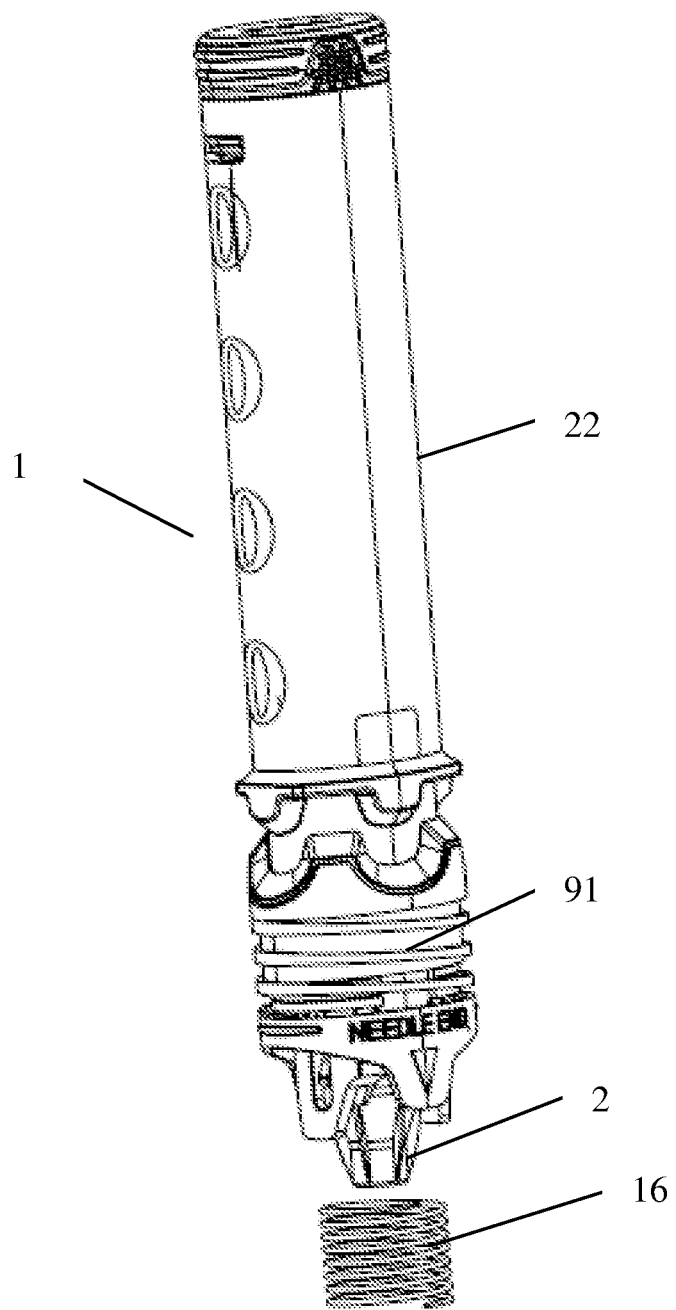
FIG. 32 shows mounting of a second biasing member over a cartridge holder of an embodiment of autoinjector described with reference to FIG. 16 to FIG. 24.
Figure 33:
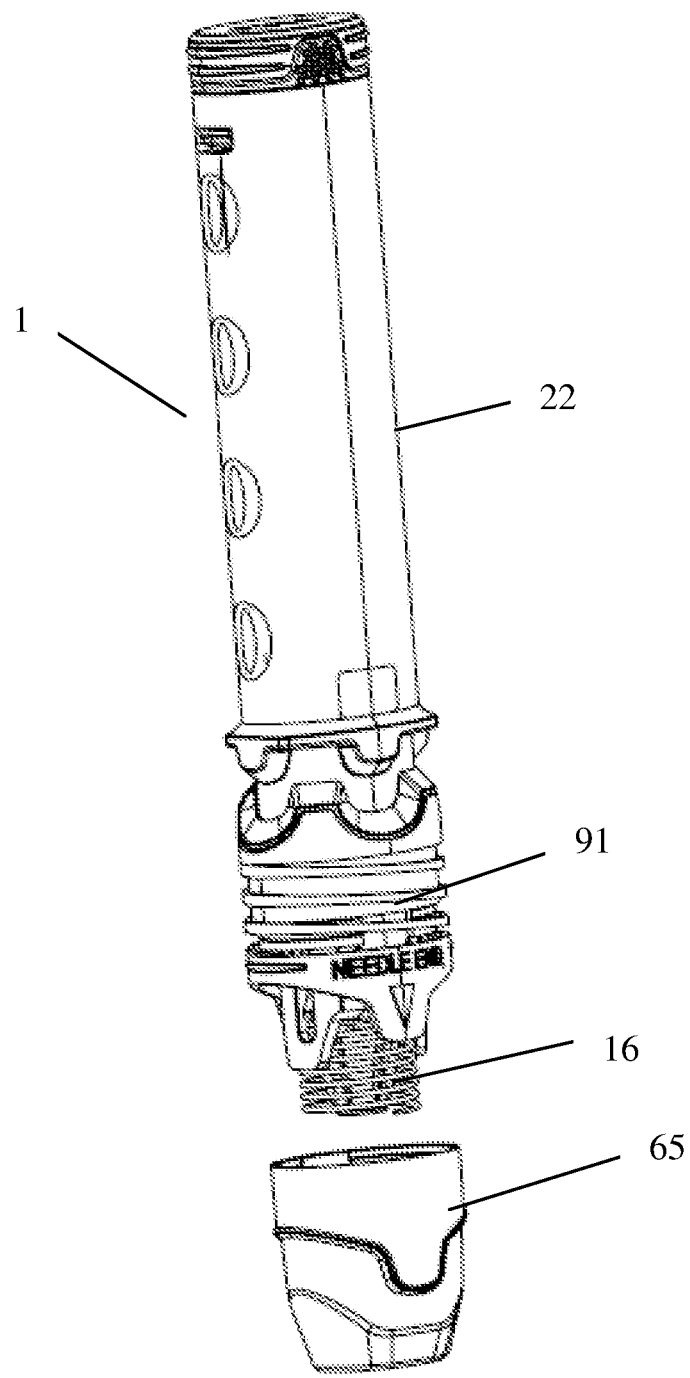
FIG. 33 shows mounting of a needle cover bottom over a second biasing member of an embodiment of autoinjector described with reference to FIG. 16 to FIG. 24.

Yet another embodiment of an autoinjector 59 may be described with reference to FIG. 3A, FIG. 27A, FIG. 27B, FIG. 27C and FIG. 28A, FIG. 28B. Except for differences described, this embodiment includes all the components described in the embodiment of FIG. 1 to FIG. 13 and hereby incorporated by reference in its entirety. Modifications and variations to the components are further discussed in this embodiment. FIG. 27A shows a front view of yet another embodiment of an autoinjector wherein a sleeve 93 is provided over a housing and the sleeve 93 and needle cover 4 are in the first locking/initial position; FIG. 27B is a side view of FIG. 27A showing a sleeve 93 provided over a housing and the sleeve 93 and needle cover 4 are in the first locking/initial position; FIG. 27C is a perspective view of FIG. 27A showing a sleeve 93 provided over housing and the sleeve 93 and needle cover 4 are in the first locking/initial position; FIG. 28A is a front view of a sleeve 93; FIG. 28B is a perspective view of a sleeve 93 of FIG. 28A.

Referring to FIG. 3A and FIGS. 28A and 28B, in this embodiment, the sleeve 93 may be an over moulded component comprising an inner sleeve 93a and an outer sleeve 93b. In this embodiment inner sleeve 93a and outer sleeve 93b combination replaces the needle cover top 64. The inner sleeve 93a and an outer sleeve 93b are arranged coaxially and concentrically. The concentrically arranged inner sleeve 93a and outer sleeve 93b may be joined together with extending elastomeric parts 101a, 101b, 101c and 101d as shown in FIG. 28B. Further ribs may be provided on the outer surface of the inner sleeve 93a and grooves on the inner surface of the outer sleeve 93b. This rib and groove engagement between the inner sleeve 93a and the outer sleeve 93b is an almost friction free engagement that helps in movement of inner sleeve 93a and outer sleeve 93b. The functioning of the sleeve 93 may be explained as follows.

The engagement of outer sleeve 93b and the needle cover bottom 65 may be as follows. Referring to FIG. 3A of aforementioned embodiment, a plurality of ribs 67a extends along the inner circumference of needle cover bottom 65 from proximal end to distal end. Similarly, a plurality of ribs 66a extends along the inner circumference of outer sleeve 93b. Ribs and grooves of outer sleeve 93b and the needle cover bottom 65 are in proper orientation. This ensures proper engagement of outer sleeve 93b and the needle cover bottom 65.

If the user grips and applies load on the outer sleeve 93b, by virtue of rib and groove engagement between the inner sleeve 93a and outer sleeve 93b, will help in moving the inner sleeve 93a upward to actuate the device, by stretching of the elastomeric part 101a, 101b, 101c and 101d, as the outer sleeve 93b will be held stationary. During the extension stage of the sleeve 93, outer sleeve 93b moves forward along with the needle cover bottom 65 by the relaxation of the second biasing member 16.

Some examples disclose the needle cover 4 comprises a sleeve 93 and a needle cover bottom 65; the sleeve 93 comprises an inner sleeve 93a and an outer sleeve 93b.

Some examples disclose the sleeve 93 comprises a proximal end 98, a distal end 99 and a tubular body 100 extending between them.

FIGS. 29 to 33 describe assembly of needle locking mechanism 60 including the sleeve 91 or sleeve 92 though the FIGS. 29 to 33 relate to the autoinjector 59 of FIGS. 16 to 24 relating to sleeve 91. Referring to FIGS. 29 to 33, the needle cover top 64 may be positioned over second sleeve section 25 of housing 1. In the next step the cam follower 14 may be positioned on the corresponding cam profile 13 such that cam follower button 38 may securely be placed on the proximal portion of angled contour surface 47. The proximal end of sleeve 91 or sleeve 92 may be affixed into the outer surface of the needle cover top 64 and the stopping ridge 97 (shown in FIG. 18A) prevent that the sleeve 91 or sleeve 92 do not extend beyond the outer periphery of needle cover top 64. After fixing the sleeve 91 or 92, the second biasing member 16 may be positioned. Finally the needle cover bottom 65 may be positioned.

Some of the embodiments of autoinjector 59 disclose wherein the cam profile 13 comprises an angled contour surface 47 in the proximal portion and cylindrical contour surface 42a in the distal portion.

Some of the embodiments of autoinjector disclose wherein the cam follower button 38 of the cam follower 14 mates with cylindrical contour surface 48a of the cam profile 13 in the second locking position 18.

Some of the embodiments of autoinjector 59 disclose wherein various medicaments may be administered. Some of the embodiments of the autoinjector 59 are particularly suitable for the administration of medicaments such as dihydroergotamine or epinephrine.

Various modifications and variations to the above described autoinjector of the various embodiments can be made without departing from the scope of the present application. It is intended that the present application encompasses all such modifications.

We claim:
1. An autoinjector for administering a fluid medicament to a subject comprising:
(i) a housing having a proximal portion and a distal portion;
(ii) a cartridge holder received within the housing, said cartridge holder having a proximal end and a distal end;
(iii) a cartridge;
(iv) a plunger;
(v) a needle cover, wherein the housing is at least partially received within the needle cover, wherein the needle cover has an inner surface;
(vi) a needle cover locking mechanism having a first locking position and a second locking position, wherein the needle cover locking mechanism comprises a cam profile and a cam follower and wherein the cam follower of the locking mechanism is located between the needle cover and the distal portion of the housing in both the first locking position and the second locking position.

2. The autoinjector of claim 1, wherein the proximal portion of the housing has a first sleeve section and the distal portion of the housing has a second sleeve section.

3. The autoinjector of claim 2, wherein the second sleeve section at a distal end of the housing comprises diametrically opposite cutting arms having flank surfaces.

4. The autoinjector of claim 3, wherein the flank surfaces of the cutting arms comprise a cam profile.

5. The autoinjector of claim 1, wherein the cam profile comprises an angled contour surface in the proximal portion and a cylindrical contour surface in the distal portion.

6. The autoinjector of claim 5, wherein a cam follower button of a cam follower mates with a distal portion of the angled contour surface of the cam profile in the first locking position.

7. The autoinjector of claim 6, wherein the cam follower button of the cam follower mates with the cylindrical contour surface of the cam profile in the second locking position.

8. The autoinjector of claim 1, wherein the cam follower comprises a cam follower protrusion on the distal portion; a cam follower button on the proximal portion; and a cam follower body extending between them.

9. The autoinjector of claim 8, wherein the protrusion of the cam follower mates with a groove on the inner surface of the needle cover both in the first locking position and in the second locking position.

10. The autoinjector of claim 1, wherein the distal end of the cartridge holder abuts the inner surface of needle cover in the first locking position.

11. The autoinjector of claim 1, wherein the needle cover further comprises a sleeve.

12. The autoinjector of claim 11, wherein the sleeve is received on an outer surface of the needle cover, wherein the sleeve prevents obstruction of movement of the needle cover from the first locking position to the second locking position when a user accidentally holds the needle cover during actuation of the autoinjector.

13. The autoinjector of claim 11, wherein the sleeve comprises a proximal end, a distal end and a coil body extending between them.

14. An autoinjector for administering a fluid medicament to a subject comprising: (i) a housing having a proximal portion and a distal portion, said housing comprises a first sleeve section and a second sleeve section, wherein the first sleeve section having inward transverse projections on the inner surface; (ii) a cartridge holder having a proximal end and a distal end, said cartridge holder received within the housing; (iii) a cartridge; (iv) a plunger having two wings provided on the outer surface, said wings having distal surfaces, wherein the distal surfaces of the wings engage the inward transverse projections of the housing at the end of medicament administration which prevents the plunger from hitting the cartridge and no stress occurs on the cartridge; (v) a needle cover, wherein the housing is at least partially received within the needle cover, (vi) a needle cover locking mechanism having a first locking position and a second locking position, said needle cover locking mechanism comprises a cam profile and a cam follower, wherein the cam follower of the locking mechanism is located between the needle cover and the second sleeve section of the housing in both the first locking position and the second locking position, wherein the needle cover further comprising a sleeve received on an outer surface of the needle cover, wherein the sleeve prevents obstruction of movement of the needle cover from the first locking position to the second locking position when a user accidentally holds the needle cover during actuation of the autoinjector.

15. The autoinjector of claim 14, wherein the sleeve comprises a proximal end, a distal end and a coil body extending between them.

* * * * *